United States Patent
Sakaguchi

(10) Patent No.: US 11,202,612 B2
(45) Date of Patent: Dec. 21, 2021

(54) MEDICAL IMAGE-PROCESSING APPARATUS, X-RAY CT APPARATUS, AND MEDICAL IMAGE-PROCESSING METHOD PERFORMING FLUID ANALYSIS TO SWITCH DISPLAYED COLOR INFORMATION

(71) Applicant: CANON MEDICAL SYSTEMS CORPORATION, Otawara (JP)

(72) Inventor: Takuya Sakaguchi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 451 days.

(21) Appl. No.: 15/824,187

(22) Filed: Nov. 28, 2017

(65) Prior Publication Data

US 2018/0146941 A1 May 31, 2018

(30) Foreign Application Priority Data

Nov. 28, 2016 (JP) .............................. JP2016-230530
Nov. 21, 2017 (JP) .............................. JP2017-223826

(51) Int. Cl.
*A61B 6/00* (2006.01)
*A61B 6/03* (2006.01)
*H05G 1/26* (2006.01)

(52) U.S. Cl.
CPC ............ *A61B 6/504* (2013.01); *A61B 6/5217* (2013.01); *A61B 6/5229* (2013.01); *A61B 6/032* (2013.01);
(Continued)

(58) Field of Classification Search
CPC ........... A61B 6/46; A61B 6/461; A61B 6/463; A61B 6/464; A61B 6/48; A61B 6/50;
(Continued)

(56) References Cited

U.S. PATENT DOCUMENTS 8,548,778 B1  10/2013  Hart et al.
2008/0303818 A1  12/2008  Moriya
(Continued)

FOREIGN PATENT DOCUMENTS

JP  2008/302090 A  12/2008
JP  2013-010005 A  1/2013
(Continued)

OTHER PUBLICATIONS

Bjarne L. Norgaard, et al. "Diagnostic Performance of Noninvasive Fractional Flow Reserve Derived From Coronary Computed Tomography Angiography in Suspected Coronary Artery Disease", Journal of the American College of Cardiology, vol. 63, No. 12, 2014, 11 pages.

(Continued)

*Primary Examiner* — Anastasia Midkiff
(74) *Attorney, Agent, or Firm* — Oblon, McClelland, Maier & Neustadt, L.L.P.

(57) ABSTRACT

A medical image-processing apparatus according to embodiments includes processing circuitry. The processing circuitry is configured to acquire image data including a blood vessel of a subject. The processing circuitry is configured to acquire an index value relating to blood flow at each position of the blood vessel by performing fluid analysis of a structure of the blood vessel included in the acquired image data. The processing circuitry is configured to acquire information indicating a display condition of the index value, as switching information to switch a display mode at displaying the index value. The processing circuitry is configured to generate a result image in which pixel values reflecting the index value are assigned in a display mode according to the switching information, for an image indicating a blood vessel of the subject. The processing circuitry is configured to cause a display to display the result image.

19 Claims, 14 Drawing Sheets

(52) U.S. Cl.
CPC ............ *A61B 6/4007* (2013.01); *A61B 6/4064* (2013.01); *H05G 1/265* (2013.01)

(58) Field of Classification Search
CPC ......... A61B 6/504; A61B 6/52; A61B 6/5211; A61B 6/5217; A61B 6/5229; A61B 6/5294; A61B 2576/00; A61B 2576/02; A61B 2576/023; A61B 2576/026; H04N 5/23222; H04N 5/23229; H04N 5/23232; H04N 5/32; H04N 5/335; G06T 1/0007; G06T 5/00; G06T 5/50; G06T 7/00; G06T 7/0012; G06T 7/0014; G06T 7/10; G06T 7/136; G06T 7/174; G06T 7/194; G06T 7/269; G06T 7/90; G06T 11/00; G06T 11/001; G06T 11/003; G06T 11/008; G06T 15/005; G06T 15/02; G06T 15/04; G06T 15/08; G06T 19/20; G06T 2207/10072; G06T 2207/10076; G06T 2207/10081; G06T 2207/10116; G06T 2207/20092; G06T 2207/20104; G06T 2207/20112; G06T 2207/20172; G06T 2207/30; G06T 2207/30004; G06T 2207/30016; G06T 2207/30048; G06T 2207/30101; G06T 2207/30104; G06T 2210/41; G06T 2211/40; G06T 2211/404; G06T 2211/22192; G06T 2211/2012; G06T 2211/2024
See application file for complete search history.

(56) References Cited

U.S. PATENT DOCUMENTS

| | | | | |
|---|---|---|---|---|
| 2011/0319752 | A1* | 12/2011 | Steinberg | A61B 6/12 600/424 |
| 2012/0063663 | A1* | 3/2012 | Kawasaki | G06T 7/0014 382/133 |
| 2012/0150516 | A1 | 6/2012 | Taylor et al. | |
| 2013/0064438 | A1 | 3/2013 | Taylor et al. | |
| 2013/0066618 | A1 | 3/2013 | Taylor et al. | |
| 2013/0151163 | A1 | 6/2013 | Taylor et al. | |
| 2013/0211728 | A1 | 8/2013 | Taylor et al. | |
| 2014/0316758 | A1* | 10/2014 | Yagi | A61B 5/7275 703/9 |
| 2014/0350393 | A1* | 11/2014 | Ichihara | A61B 5/029 600/425 |
| 2015/0038860 | A1* | 2/2015 | Fonte | A61B 6/50 600/505 |
| 2015/0161790 | A1* | 6/2015 | Takahashi | A61B 5/0245 600/424 |
| 2015/0245776 | A1* | 9/2015 | Hirohata | A61B 6/032 600/504 |
| 2015/0327780 | A1* | 11/2015 | Kano | A61B 5/026 600/407 |
| 2017/0071479 | A1 | 3/2017 | Kano et al. | |

FOREIGN PATENT DOCUMENTS

| | | |
|---|---|---|
| JP | 2013-534154 | 9/2013 |
| JP | 2015-231524 A | 12/2015 |
| JP | 2016-172003 A | 9/2016 |

OTHER PUBLICATIONS

Japanese Office Action dated Jun. 29, 2021, issued in Japanese Patent Application No. 2017-223826.

* cited by examiner

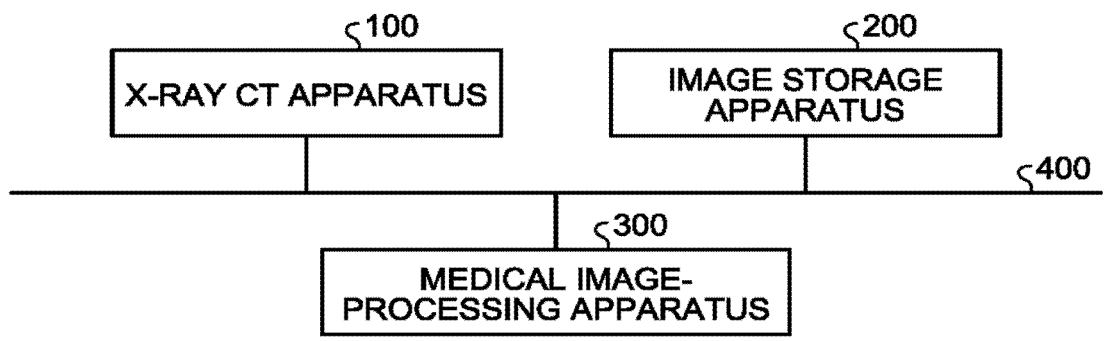
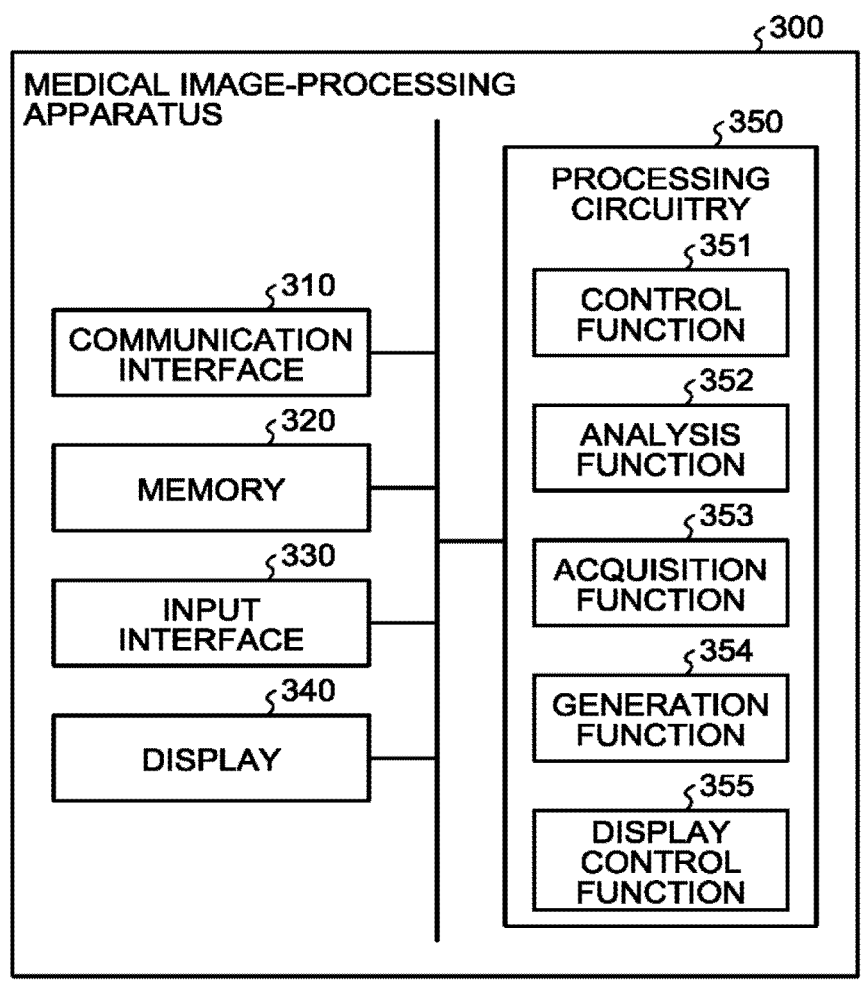

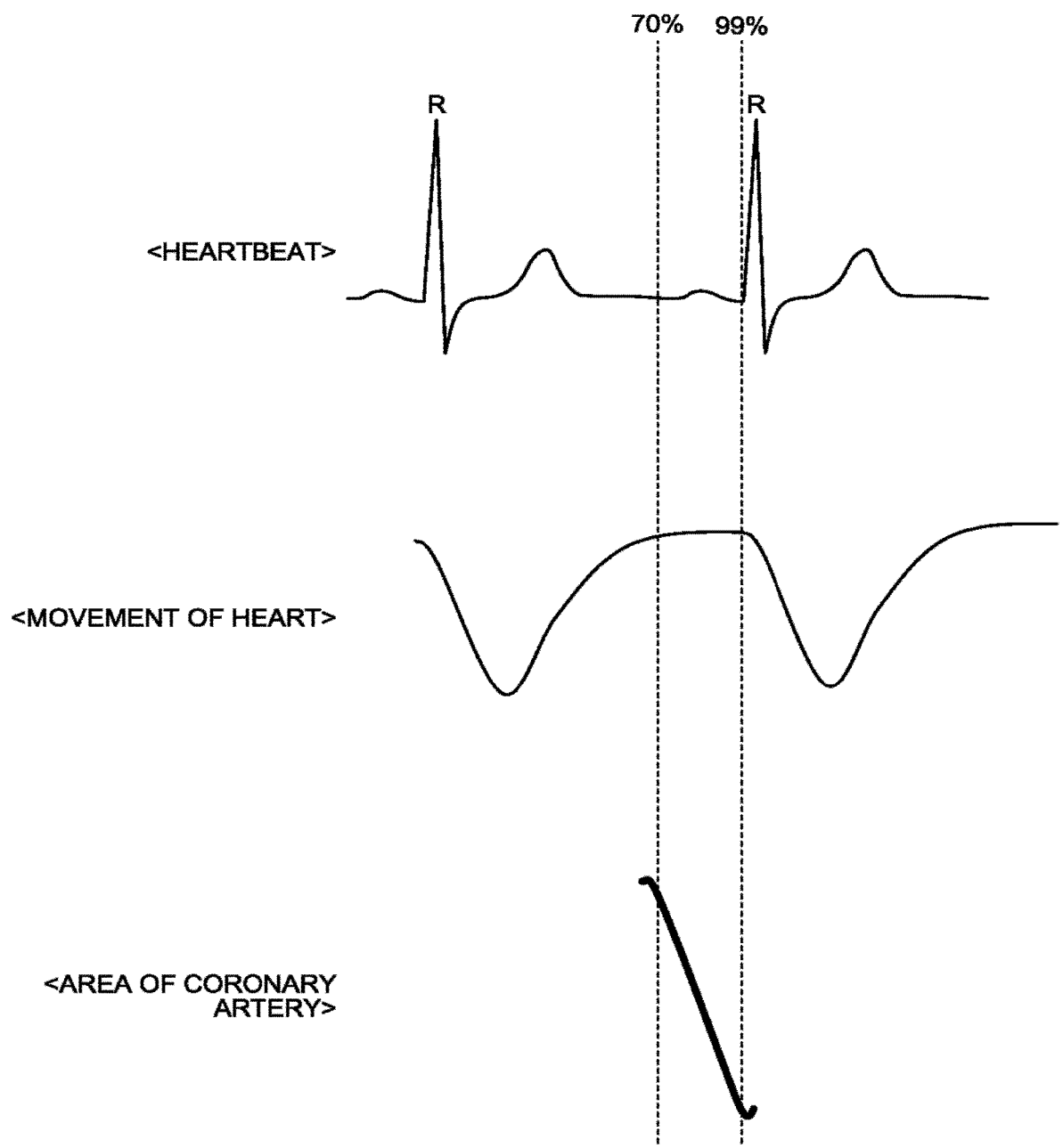

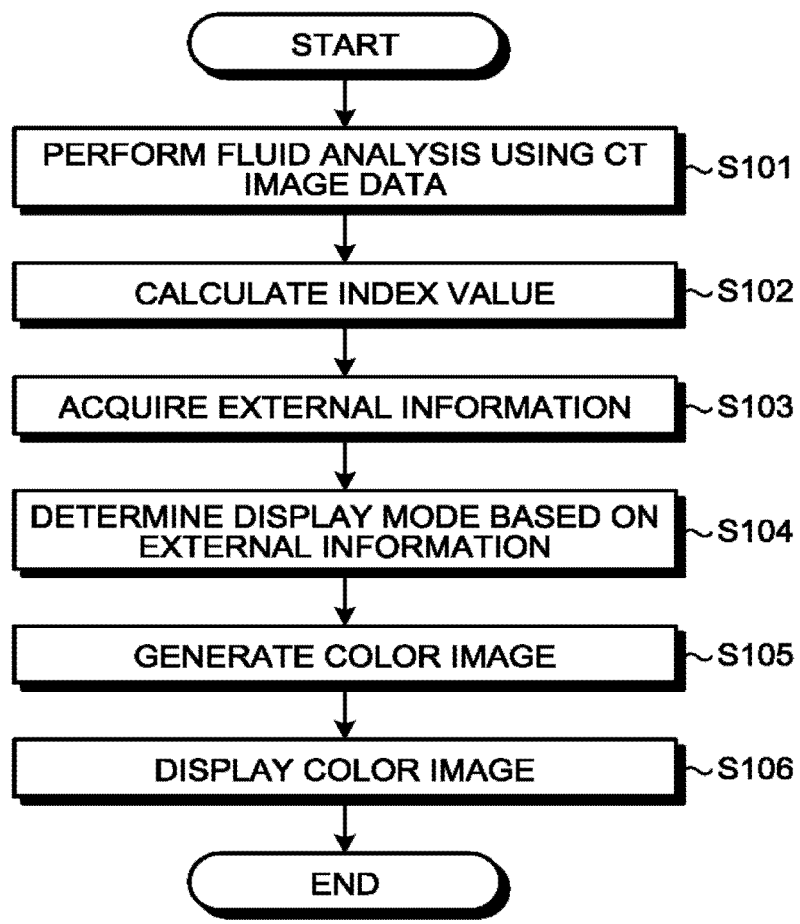

MEDICAL IMAGE-PROCESSING APPARATUS, X-RAY CT APPARATUS, AND MEDICAL IMAGE-PROCESSING METHOD PERFORMING FLUID ANALYSIS TO SWITCH DISPLAYED COLOR INFORMATION

CROSS-REFERENCE TO RELATED APPLICATIONS

This application is based upon and claims the benefit of priority from Japanese Patent Application No. 2016-230530, filed on Nov. 28, 2016 and Japanese Patent Application No. 2017-223826, Filed on Nov. 21, 2017; the entire contents of which are incorporated herein by reference.

FIELD

The embodiments described herein relate generally to a medical image-processing apparatus, an X-ray computerized-tomography (CT) apparatus, and a medical image-processing method.

BACKGROUND

It has been known that causes of ischemic diseases of organs include, broadly classified, a disruption of blood circulation and a functional disorder of an organ itself. For example, stenosis that is one example of the disruption of blood circulation in a coronary artery is a serious lesion lead to an ischemic heart disease, and in this kind of ischemic heart disease, it is necessary to determine whether to treat by medication or to treat by stent placement, or the like. In recent years, a method of measuring fractional flow reverse (FOR) by using a pressure wire in coronary angiography (CAG) by catheters has been recommended as a diagnosis for hematogenous ischemia evaluation in coronary arteries.

On the other hand, for example, a method of non-invasively performing hematogenous ischemia evaluation of coronary arteries by using medical images of a heart collected by a medical diagnostic-imaging apparatus, such as an X-ray CT apparatus, a magnetic resonance imaging (MRI) apparatus, and an ultrasonography apparatus, has also been known. As described above, the hematogenous ischemia evaluation has been performed by various methods and a treatment according to the evolution has been performed, and in recent years, it is desired to determine a practical effect of the treatment before actually performing the treatment.

BRIEF DESCRIPTION OF THE DRAWINGS

FIG. 1 shows one example of a configuration of a medical image-processing system according to a first embodiment;

FIG. 2 shows one example of a configuration of a medical image-processing apparatus according to the first embodiment;

FIG. 4 is a diagram for explaining temporal phases in fluid analysis according to the first embodiment;

FIG. 10 is a flowchart showing a procedure of processing performed by the medical image-processing apparatus according to the first embodiment;

DETAILED DESCRIPTION

Figure 3:
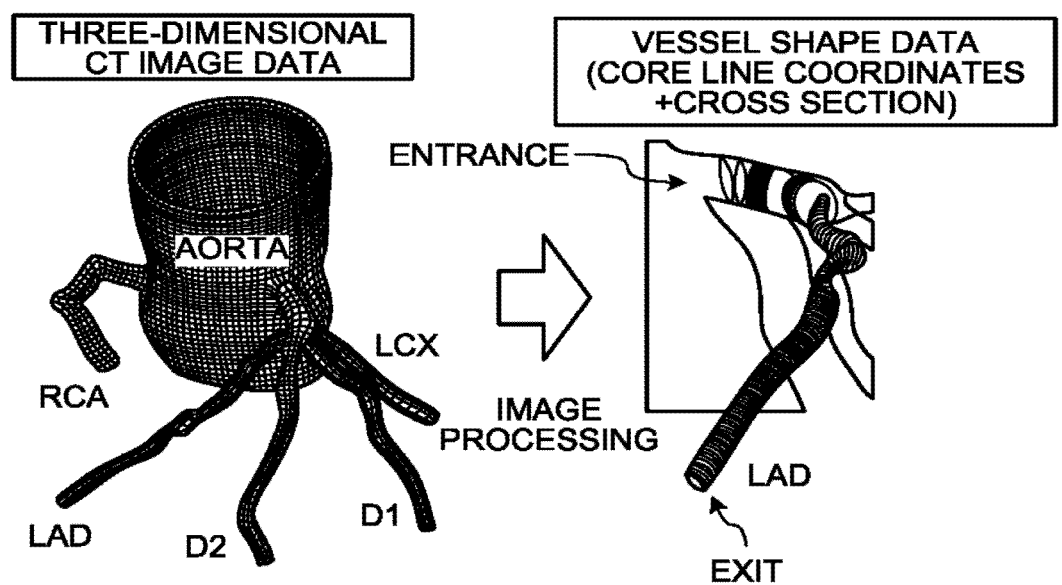
FIG. 3 is a diagram for explaining one example of processing performed by an analysis function according to the first embodiment.

According to an embodiment, a medical image-processing apparatus includes processing circuitry. The processing circuitry is configured to acquire image data including a blood vessel of a subject. The processing circuitry is configured to acquire an index value relating to blood flow at each position of the blood vessel by performing fluid analysis of a structure of the blood vessel included in the acquired image data. The processing circuitry is configured to acquire information indicating a display condition of the index value, as switching information to switch a display mode at displaying the index value. The processing circuitry is configured to generate a result image in which pixel values reflecting the index value are assigned in a display mode according to the switching information, for an image indicating a blood vessel of the subject. The processing circuitry is configured to cause a display to display the result image.

Embodiments of a medical image-processing apparatus, an X-ray CT apparatus, and a medical image-processing method according to the present application are explained in detail below referring to the accompanying drawings. The embodiments described below are not intended to limit the medical image-processing apparatus, the X-ray CT apparatus, and the medical image-processing method according to the present application.

First Embodiment

First, a first embodiment is explained. In the first embodiment, an example of applying a technique according to the present application to a medical image-processing apparatus is explained. Explanation is given in the following with a medical image-processing system that includes the medical image-processing apparatus as an example. Moreover, a case in which a blood vessel of a heart is a subject of analysis is explained in the following as an example.

FIG. 1 shows one example of a configuration of the medical image-processing system according to the first embodiment. As shown in FIG. 1, the medical image-processing system according to the first embodiment includes an X-ray CT apparatus 100, an image storage apparatus 200, and a medical image-processing apparatus 300.

For example, the medical image-processing apparatus 300 according to the first embodiment is connected to the X-ray CT apparatus 100 and the image storage apparatus 200 through a network 400 as shown in FIG. 1. The medical image-processing system can be connected to still another medical diagnostic-imaging apparatus, such as an MRI apparatus and a positron emission tomography (PET) apparatus, through the network 400.

The X-ray CT apparatus 100 collects CT image data (volume data) of a subject. Specifically, the X-ray CT apparatus 100 rotates an X-ray tube and an X-ray detector about the subject at substantially the center, and detects X-rays passing through the subject, and thereby collects projection data. The X-ray CT apparatus 100 then generates chronological three-dimensional CT-image data based on the collected projection data.

The image storage apparatus 200 stores image data that is collected by various kinds of medical diagnostic-imaging apparatuses. For example, the image storage apparatus 200 is implemented by a computer device such as a server device. In the present embodiment, the image storage apparatus 200 acquires the CT image data (volume data) from the X-ray CT apparatus 100 through the network 400, and causes a memory provided inside or outside of the apparatus to store the acquired CT image data.

The medical image-processing apparatus 300 acquires image data from various kinds of medical diagnostic-imaging apparatuses through the network 400, and processes the acquired image data. For example, the medical image-processing apparatus 300 is implemented by a computer device such as a workstation. In the present embodiment, the medical image-processing apparatus 300 acquires the CT image data from the X-ray CT apparatus 100 or the image storage apparatus 200 through the network 400, and performs various kinds of image processing on the acquired CT image data. The medical image-processing apparatus 300 displays the CT image data before or after the image processing on a display or the like. The medical image-processing apparatus 300 can be arranged at various places. For example, the medical image-processing apparatus 300 is arranged in a CT room in which the X-ray CT apparatus 100 is arranged, a catheter treatment room in which various treatments using catheters are performed, an interpretation room to interpret images, or the like. When arranging in more than one place, the medical image-processing apparatus 300 is arranged in each place.

FIG. 2 shows one example of a configuration of the medical image-processing apparatus 300 according to the first embodiment. For example, as shown in FIG. 2, the medical image-processing apparatus 300 includes a communication interface 310, a memory 320, an input interface 330, a display 340, and processing circuitry 350.

The communication interface 310 is connected to the processing circuitry 350, and controls transmission and communication of various kinds of data conducted between itself and various kinds of medical diagnostic-imaging apparatuses or the image storage apparatus 200 connected through the network 400. For example, the communication interface 310 is implemented by a network card, a network adapter, a network interface controller (NIC), or the like. In the present embodiment, the communication interface 310 receives the CT image data from the X-ray CT apparatus 100 or the image storage apparatus 200, and outputs the received CT image data to the processing circuitry 350.

The memory 320 is connected to the processing circuitry 350, and stores various kinds of data. For example, the memory 320 is implemented by a semiconductor memory device, such as a random-access memory (RAM) and a flash memory, a hard disk, an optical disk, or the like. In the present embodiment, the memory 320 stores the CT image data received from the X-ray CT apparatus 100 or the image storage apparatus 200. Furthermore, the memory 320 stores results of processing performed by the processing circuitry 350.

The input interface 330 is connected to the processing circuitry 350, and converts an input operation accepted from an operator into an electrical signal to output to the processing circuitry 350. For example, the input interface 330 is implemented by a trackball, a switch button, a mouse, a keyboard, a touch pad in which an input operation is made by touching an operating surface, a touch screen in which a display screen and a touch pad are integrated, a non-contact input interface using an optical sensor, a voice input interface, or the like. The input interface 330 is connected to the processing circuitry 350, and converts an input operation received from an operator into an electrical signal to output to the processing circuitry 350. The input interface 330 in this specification is not limited to one that includes a physical operating part such as a mouse and a keyboard. For example, processing circuitry that receives an electrical signal corresponding to an input operation from an external input device provided separately from the medical image-processing apparatus 300, and that outputs this electrical signal to the processing circuitry 350 is also included in examples of the input interface 330.

The display 340 is connected to the processing circuitry 350, and displays various kinds of information and image data that are output from the processing circuitry 350. For example, the display 340 is implemented by a liquid crystal monitor, a cathode ray tube (CRT) monitor, a touch panel, and the like.

The processing circuitry 350 controls the respective components included in the medical image-processing apparatus 300 according to an input operation accepted from an operator through the input interface 330. For example, the processing circuitry 350 is implemented by a processor. In the present embodiment, the processing circuitry 350 causes the memory 320 to store the CT image data that is output from the communication interface 310. Moreover, the processing circuitry 350 reads the CT image data from the memory 320 to display on the display 340.

With these components, the medical image-processing apparatus 300 enables display of a color image that facilitates observation of indexes relating to blood flow. Specifically, the medical image-processing apparatus 300 switches a display mode of a color image that reflects indexes relating to blood flow based on external information, thereby displaying a color image that facilitates observation. That is, the medical image-processing apparatus 300 enables display of a color image that is easy for an observer to observe by displaying a color image according to a situation. The external information for switching the display mode of a color image is hereinafter called switching information also.

To implement the processing described above, the processing circuitry 350 of the medical image-processing apparatus 300 according to the first embodiment performs a control function 351, an analysis function 352, an acquisition function 353, a generation function 354, and a display control function 355 as shown in FIG. 2. The processing circuitry 350 is one example of a processing circuitry in claims.

The control function 351 performs overall control of the medical image-processing apparatus 300. For example, the control function 351 controls various kinds of processing according to an electrical signal that is received from the input interface 330. As one example, the control function 351 controls acquisition of CT image data through the communication interface 310, storage of acquired CT image data in the memory 320, and the like. Furthermore, for example, the control function 351 reads CT image data stored in the memory 320, and controls generation of a display image from the read CT image data. As one example, the control function 351 generates an image of a blood vessel by subjecting CT image data to various kinds of image processing. For example, the control function 351 generates a clinical image, such as a volume rendering image, a curved multiplanar reconstruction (CPR) image, a multiplanar reconstruction (MPR) image, and a stretched multiplanar reconstruction (SPR) image, by performing image processing on CT image data. Moreover, for example, the control function 351 generates a model image of a blood vessel that is included in CT image data by subjecting the CT image data to image processing.

The analysis function 352 performs fluid analysis based on CT image data. Specifically, the analysis function 352 performs fluid analysis on a structure of a blood vessel that is included in acquired image data, and acquires index values relating to blood flow at each position of the blood vessel. More specifically, the analysis function 352 first extracts chronological vessel shape data that shows the shape of a blood vessel from three-dimensional CT image data. For example, the analysis function 352 reads CT image data of multiple temporal phases collected chronologically from the memory 320, and performs image processing on the read CT image data of multiple temporal phases, thereby extracting chronological vessel shape data.

The analysis function 352 sets a target region for which an index relating to blood flow is calculated in a blood vessel region included in the CT image data. Specifically, the analysis function 352 sets a target region in a blood vessel region according to an instruction or image processing made through the input interface 330 by an operator. The analysis function 352 then extracts, for example, a core line (coordinate information of a core line) of the blood vessel, a cross-sectional area of the blood vessel or a lumen on a cross section perpendicular to the core line, a distance from the core line to an internal wall in a cylindrical direction on a cross section perpendicular to the core line, a distance form the core line to an external wall, and the like from the CT image data as the vessel shape data of the set target region. The analysis function 352 can extracts various other vessel shape data according to an analysis method.

Furthermore, the analysis function 352 sets analysis conditions for the fluid analysis. specifically, the analysis function 352 sets physical properties of blood, conditions for iterative calculation, initial values of the analysis, and the like as the analysis conditions. For example, the analysis function 352 sets the viscosity, density, and the like of blood as the physical properties of blood. Moreover, the analysis function 352 sets maximum iteration, a relaxation coefficient, a residual tolerance, and the like in the iterative calculation as the conditions for the iterative calculation. Furthermore, the analysis function 352 sets initial values of flow rate, pressure, fluid resistance, pressure boundary, and the like as the initial values of the analysis. Various kinds of values used by the analysis function 352 can be programmed in advance in the system, or can be defined by an operator dialogically.

The analysis function 352 calculates indexes relating to blood flow of a blood vessel by the fluid analysis using image data that includes the blood vessel (for example, coronary artery or the like). Specifically, the analysis function 352 performs the fluid analysis using the vessel shape data and the analysis conditions, to calculate the indexes relating to blood flow in a target region of the blood vessel. For example, the analysis function 352 calculates indexes, such as pressure, flow rate of blood, flow speed of blood, vector, and shearing stress, at each predetermined position of the blood vessel based on the vessel shape data, such as an outline of a lumen or an external wall, and a cross-sectional area and a core line of the blood vessel, the physical properties of the blood, the set conditions, such as the conditions for iterative calculation, and initial values of the analysis. Furthermore, the analysis function 352 calculates temporal variations in indexes, such as pressure, flow rate of blood, flow speed of blood, vector, and shearing stress, by using temporal variations in the vessel shape data, such as an outline of a lumen or an external wall, and a cross-sectional area and a core line of the blood vessel.

FIG. 3 is a diagram for explaining one example of processing performed by the analysis function 352 according to the first embodiment. As shown in FIG. 3, for example, the analysis function 352 extracts the vessel shape data for a target region LAD from three-dimensional CT image data that includes an aorta and a coronary artery. Moreover, the analysis function 352 sets the analysis conditions for analysis of the extracted LAD. The analysis function 352 then performs the fluid analysis using the extracted vessel shape data of LAD and the set analysis conditions, thereby calculating indexes, such as pressure, flow rate of blood, flow speed of blood, vector, and shearing stress, for each predetermined position along the core line, for example, from a boundary of the entrance of the target region LAD to a boundary of the exit. That is, the analysis function 352 calculates distributions of pressure, flow rate of blood, flow speed of blood, vector, a shearing stress, and the like of the target region.

As described above, the analysis function 352 extracts respective vessel shape data from CT image data of multiple temporal phases collected over time, and performs the fluid analysis using the extracted vessel shape data of the multiple temporal phases and the analysis conditions, thereby calculating the indexes relating to blood flow. The analysis function 352 acquires a highly accurate analysis result by using CT image data of multiple temporal phases within a predetermined cardiac phase range.

The fluid analysis by the analysis function 352 is not limited to fluid analysis using the analysis conditions as described above. For example, the analysis function 352 can also calculate the indexes relating to blood flow using machine learning. When the indexes relating to blood flow are calculated using machine learning, for example, the analysis function 352 stores a large number of blood flow index distributions when blood flows to a simulated part simulating the shape of a part of a blood vessel in the memory 320 and performs learning. Specifically, the analysis function 352 performs fluid analysis using boundary conditions on the entrance side of the simulated part, boundary conditions on the exit side of the simulated part, and the shape of the simulated part in advance. Furthermore, the analysis function 352 generates a discriminator that derives the blood flow index distribution from the shape of the simulated part and the boundary conditions by storing relationship between the shape of the simulated part, the boundary conditions and the blood flow index distribution in the memory and performing learning. The analysis function 352 performs the above-described storing and learning for simulated parts with various shapes and various boundary conditions. When a blood vessel shape data and boundary conditions of a subject are inputted, the analysis function 352 derives the blood flow index distribution in the blood vessel shape data of the subject by inputting the blood vessel shape data to the discriminator.

FIG. 4 is a diagram for explaining temporal phases used in the fluid analysis according to the first embodiment. In FIG. 4, an upper portion shows heartbeats, a central portion shows movement of heart, and a lower portion shows an area of a coronary artery. Moreover, a horizontal direction is for time in FIG. 4, and temporal variations in heartbeats, movement of heart, and area of coronary artery are associated therewith. For example, the analysis function 352 performs the fluid analysis using CT image data of cardiac phases that are included in a range of 70% to 90% of cardiac phase. The cardiac phases 70% to 90% are temporal phases in which the movement of the heart is not favorable, and variations in area of the coronary artery is large. Hearts move by contraction and expansion, and the movement becomes stable in a latter half period of an expanding period (range of 70% to 90% of cardiac phase) as shown in the central portion in FIG. 4. That is, the analysis function 352 can use CT image data in which movement occurring with heartbeats is small, by using CT image data of a cardiac phase that is included in this range of 70% to 90% of cardiac phase in which movement is stable.

Moreover, as shown in the lower portion in FIG. 4, the area of the coronary artery is largest at around 70% cardiac phase, and becomes smallest at around 99%. This is because, blood starts flowing into the coronary artery at around 70% cardiac phase, and blood flows out as the phase proceeds toward 99%. The analysis function 352 acquires further highly accurate analysis result by using CT image data of multiple temporal phases in the range of 70% to 90% of cardiac phase such that this variation in area of the coronary artery is included as much as possible.

Furthermore, the analysis function 352 calculates a fractional flow reserve (FFR) based on the distribution of pressure in the target region. That is, the analysis function 352 calculates an FFR that is an index to estimate to what extent the blood flow is impaired by a lesion, based on pressure on an upstream side and pressure on a downstream side of a predetermined position in a blood vessel (for example, a portion of lesion such as stenosis and plaque). The analysis function 352 according to the present application can calculate various pressure indexes as the FFR.

First, the definition of the FFR is explained. As described above, the FFR is an index to estimate to what extent the blood flow is impaired by a lesion (for example, stenosis, plaque, and the like), and is defined by a ratio between a flow rate without lesion and a flow rate with a lesion. It is calculated by Equation (1) below. "Qn" in Equation (1) indicates a flow rate without lesion, and "Qs" indicates a flow rate with a lesion.

$$FFR \equiv \frac{Qs}{Qn} \quad (1)$$

The FFR is defined by an expression of dividing "Qs" by "Qn" as expressed in Equation (1). In calculation of FFR, a flow rate and pressure are brought into a proportional relationship by inducing a maximum congestive state (stressed state) giving adenosine to a subject generally, and the definition of pressure can be thereby substituted for the FFR. That is, by making the flow rate and pressure inside a blood vessel proportional, Equation (1) can be expressed as Equation (2). "Pa" in Equation (2) indicates pressure on an upstream side of a lesion, and "Pd" indicates pressure on a downstream side of the lesion. Moreover, "Pv" indicates pressure of a right atrium into which venous blood flows from the entire body.

$$FFR \equiv \frac{Qs}{Qn} = \frac{Pd - Pv}{Pa - Pv} \quad (2)$$

For example, by making the relationship between a flow rate and pressure inside a blood vessel proportional, "Qs" can be expressed as "Pd−Pv", and "Qn" can be expressed as "Pa−Pv" as shown in Equation (2). That is, the FFR is expressed by a ratio of values obtained by subtracting baseline pressure from pressure on an upstream side and pressure on a downstream side of a lesion, respectively.

In the stressed state in which adenosine is given to a subject, it can be regarded as "Pa>>Pv" and "Pd>>Pv", and therefore, Equation (2) can be regarded as in Equation (3) below.

$$FFR \equiv \frac{Qs}{Qn} = \frac{Pd - Pv}{Pa - Pv} \approx \frac{Pd}{Pa} \quad (3)$$

That is, as shown in Equation (3), the FFR is calculated by an expression of dividing "Pd" by "Pa". For example, the analysis function 352 calculates a value of FFR at each position of the blood vessel by substituting the calculated pressure on the upstream side and pressure on the downstream side of the lesion into Equation (3) above.

The above-described the calculation method of FFR value is merely an example, and FFR value according to the present embodiment is not limited to one using the above-described method. That is, FFR value according to the present embodiment may be any kind as long as it is a pressure index value indicating a comparison between a pressure at a point on upstream side of a blood vessel and a pressure at a point on downstream side of the blood vessel. For example, FFR value according to the present embodiment may be a pressure ratio calculated in a subject in a resting state. Also, FFR value according to the present embodiment may be a pressure ratio based on a pressure value (at least one of a pressure value on upstream side and a pressure value on downstream side) estimated using another value. Furthermore, FFR value according to the present embodiment may be a pressure ratio based on a pressure value (at least one of a pressure value on upstream side and a pressure value on downstream side) replaced with another value.

Hereinafter, the respective pressure indexes described above are collectively termed as FFR.

Figure 5A:
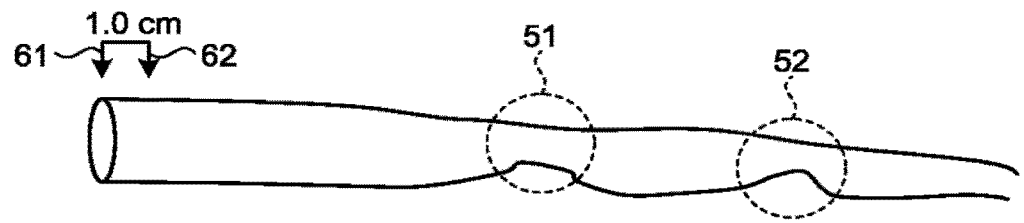
FIG. 5A is a diagram for explaining a calculation example of ΔFFR by the analysis function according to the first embodiment.
Figure 5B:
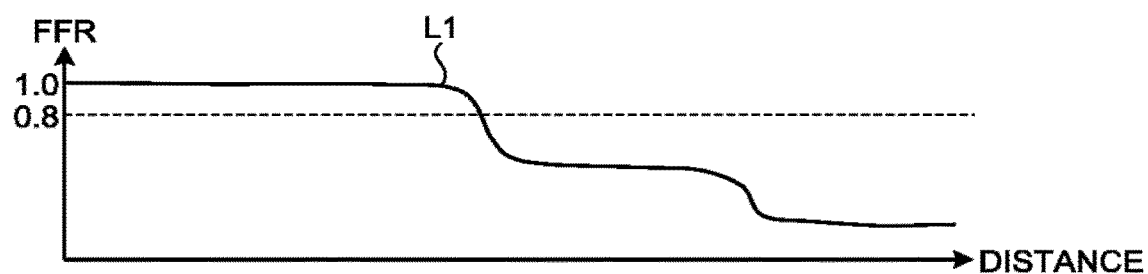
FIG. 5B is a diagram for explaining a calculation example of ΔFFR by the analysis function according to the first embodiment.
Figure 5C:
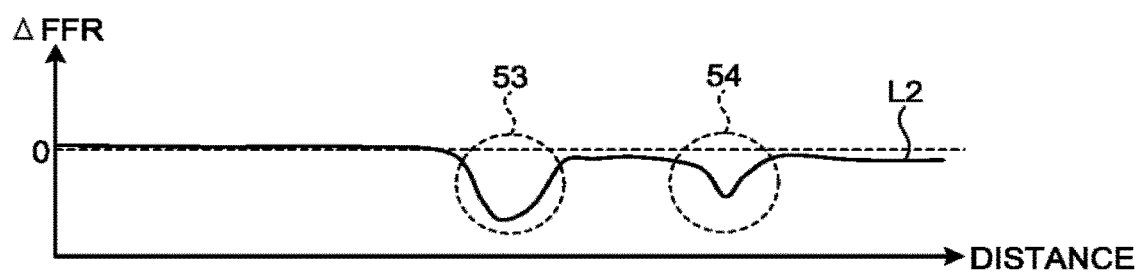
FIG. 5C is a diagram for explaining a calculation example of ΔFFR by the analysis function according to the first embodiment.

Moreover, the analysis function 352 calculates ΔFFR that is obtained by subtraction between FFR values of respective positions calculated as described above. FIG. 5A to FIG. 5C are diagrams for explaining a calculation example of ΔFFR by the analysis function 352 according to the first embodiment. FIG. 5A shows a blood vessel for which ΔFFR is calculated, and a calculation width of ΔFFR for the blood vessel. Furthermore, FIG. 5B shows a graph of FFR in the blood vessel shown in FIG. 5A. FIG. 5C shows one example of ΔFFR that is calculated by the analysis function 352.

For example, the analysis function 352 sets the calculation width to calculate ΔFFR to "1.0 cm" for a blood vessel for which ΔFFR is calculated. The calculation width is a width to determine positions between which a difference in values of FFR is taken. For example, with the calculation width "1 cm" shown in FIG. 5A, a difference between a value of FFR at a position of an arrow 61 and a value of FFR at a position of an arrow 62 of the blood vessel is calculated. That is, the analysis function 352 calculates a difference at respective positions while shifting the calculation width shown in FIG. 5A along the blood vessel by a predetermined distance.

As one example, the analysis function 352 first calculates a difference (ΔFFR) between a value of FFR at the position of the arrow 61 and a value of FFR at the position of the arrow 62 at the position of the calculation width shown in FIG. 5A. The analysis function 352 then shifts the calculation width along the blood vessel (in a rightward direction of the drawing) by "1 mm", and calculates, at a position after the shift, a difference (ΔFFR) between a value of FFR at a position of the arrow 61 and a value of FFR at a position of the arrow 62. In the same manner, the analysis function 352 sequentially calculates ΔFFR at each position, shifting the calculation width along the blood vessel by "1 mm" each.

Thus, the analysis function 352 can acquire ΔFFR of each position (distance from a starting portion) of the blood vessel as shown in a curved line L2 in FIG. 5C. The calculation width used in calculation of ΔFFR can be arbitrarily set. For example, the analysis function 352 can extract a stenosis or a plaque from CT image data, and can set the calculation width according to the size of the extracted stenosis or plaque. As one example, the analysis function 352 sets the calculation width having a substantially the same width as the width of a stenosis or a plaque in a direction of length of a blood vessel.

As described, ΔFFR calculated by the analysis function 352 can be used to evaluate, for example, multiple stenoses as shown in FIG. 5A. For example, when a stenosis 51 and a stenosis 52 are present in a blood vessel as shown in FIG. 5A, a graph of FFR of the blood vessel shows a value of FFR decreased at a position of each stenosis as shown in a curved line L1 in FIG. 5B. If the stenosis 51 and the stenosis 52 are evaluated only with the graph of FFR shown in FIG. 5B, it is difficult to grasp which stenosis influences the blood flow more.

When the value of ΔFFR calculated by the analysis function 352 is referred to, it is possible to see that a change position 53 having a larger change in ΔFFR (value of FFR significantly decreases) influences the flow rate more out of the change position 53 and a change position 54. That is, it can be seen that the stenosis 51 corresponding to the change position 53 influences the flow rate more, and has higher priority for treatment.

Moreover, the analysis function 352 according to the first embodiment can calculate a diameter stenosis rate also, based on an internal diameter of a blood vessel. For example, the analysis function 352 calculates an inner diameter of a blood vessel at each position of the blood vessel using CT image data, and calculates the diameter stenosis rate (% DS) using the calculated inner diameter of each position.

Referring back to FIG. 2, the acquisition function 353 acquires switching information to switch a display mode at the time when an index value is displayed. Specifically, the acquisition function 353 acquires information indicating a display condition of the index value as the switching information. That is, the acquisition function 353 acquires information enabling to determine the state of displaying the index value. The switching information acquired by the acquisition function 353 is used to determine a display mode of a color image in which a value of index relating to flow rate is indicated by color information. For example, the acquisition function 353 acquires at least one of index type information, examination information, and subject information, as the switching information. Moreover, the acquisition function 353 acquires display information (for example, an image or the like) that is displayed along with the index value, or information of an application that is activated together with display of the index value, as the switching information.

The index type information includes, for example, information such as FFR, instantaneous FFR, ΔFFR, pressure, flow rate, and stenosis rate. The acquisition function 353 acquires an index value type that is specified by an operator through the input interface 330, and informs the acquired information to the generation function 354. Alternatively, the acquisition function 353 acquires a default index value type, and informs the acquired information about the type to the generation function 354.

Furthermore, the examination information includes, for example, information such as an examination type and an examination responsible person. The acquisition function 353 acquires the information about an examination type, such as whether the examination is normal or urgent, or an examination responsible doctor from information input through the input interface 330. The acquisition function 353 then informs the acquired examination information to the generation function 354. Alternatively, the acquisition function 353 acquires the examination information described above from a server device that manages a hospital information system (HIS) or a radiology information system (RIS) that is applied to the medical image processing system, and informs the acquired examination information to the generation function 354.

Moreover, the subject information includes, for example, information of the number of times the subject had this examination, past examination results, treatment history, body type information, nationality, race, residential area, belonging organization, current medications, results of medical examinations, and the like. The past examination results include, for example, information of whether a stenosis has been found in computed tomographic angiography (CTA), an area and a diameter of a blood vessel at which a stenosis has been found, a position of a stenosis (for example, whether it is a triple vessel disease in which stenoses are found in three coronary arteries), and the like. The treatment history includes, for example, information indicating whether a coronary artery bypass surgery has been done, and the like. Furthermore, the body type information includes, for example, a cardiac mass, a body weight, a body mass index (BMI), and the like. The acquisition function 353 acquires the subject information described above from information that is input through the input interface 330, and informs the acquired subject information to the generation function 354. Alternatively, the acquisition function 353 acquires the subject information described above from a server device that manages an HIS or an RIS that is applied to the medical image-processing system, and informs the acquired subject information to the generation function 354.

Moreover, the acquisition function 353 acquires, for example, information of an image to be displayed along with an index value, information of an application to be used with display of an index value, information indicating a display purpose of an index value, and the like. As one example, the acquisition function 353 acquires information of an image to be displayed on the display 340 besides the display of an index value. For example, the acquisition function 353 acquires information of a type of an image (for example, volume rendering image, MPR image, CPR image, myocardial perfusion image, or the like) to be displayed on the display 340, a part to be shown in an image (for example, an image showing an entire heart including coronary arteries, or a local image of a coronary artery), and the like. The acquisition function 353 can acquire a type or a part of image, for example, from supplementary information of image data. Furthermore, the acquisition function 353 can acquire information indicating that an image is a local image, for example, by accepting a region selecting operation with respect to the displayed image through the input interface also. Moreover, the acquisition function 353 can acquire a position in an image, for example, by accepting a position specifying operation with respect to a displayed image through the input interface also.

Furthermore, the acquisition function 353 acquires, for example, information of an application that is activated besides an application to display an index value. For example, the acquisition function 353 acquires information of an analysis application that is activated besides the application to display an index value. The information of an application acquired by the acquisition function 353 can be an application that is associated with the application to display an index value (for example, a different application that is included in the same software as the application to display an index value), or can be an application that is not associated with the application to display an index value (for example, an application that is included in different software from the application to display an index value).

Moreover, the acquisition function 353 acquires, for example, the information indicating a display purpose of an index value from an application. As one example, the acquisition function 353 acquires a display purpose of an index based on an operation in an application different from the application to display an index value. An example of showing a display purpose of an index value is described in detail later.

The generation function 354 generates a color image in which an index value is reflected in a display mode according to the switching information, for an image showing a blood vessel of a subject. Specifically, the generation function 354 generates a color image in which an index value is reflected in a display mode according to a condition of displaying an index value. That is, the generation function 354 generates a color image based on a color table that is set according to a condition of displaying an index value. For example, the generation function 354 generates a color image in which an index value is reflected in a display mode according to at least one of information out of the type information, the examination information, and the subject information of an index value. That is, the generation function 354 determines a display mode of a color image based on the switching information that has been informed from the acquisition function 353, and generates a color image in the determined display mode. In the following, a color image that is generated by the generation function 354 is explained using FIG. 6A to FIG. 6F. FIG. 6A to FIG. 6F show one example of a color image that is generated by the generation function 354 according to the first embodiment.

Figure 6A:
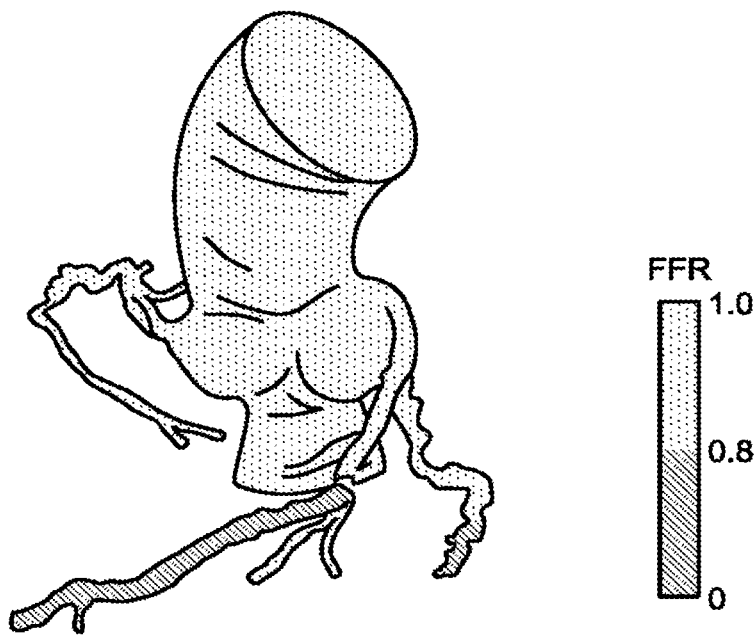
FIG. 6A shows one example of a color image that is generated by a generation function according to the first embodiment.

For example, the generation function 354 sets a reference value for the index value according to the switching information, and generates a color image in which the color changes at the set reference value as a boundary. As one example, the generation function 354 sets "0.8" as the reference value of FFR as shown in FIG. 6A, and generates a two-color image in which the color changes at the set reference value "0.8" as a boundary. That is, the generation function 354 classifies values of FFR analyzed by the analysis function 352 for each position of a coronary artery of a subject into two ranges based on "0.8" as a boundary. The generation function 354 then determines a color of each of the two ranges (for example, red for values smaller than 0.8 and blue for values equal to or larger than 0.8, or the like), and generates a color image in which each position in a model image of a blood vessel of the subject is colored with the determined color. Thus, the generation function 354 generates a color image that enables to recognize a region in which a value of FFR is smaller than "0.8" at a glance. As a result, an observer can make diagnosis whether to perform percutaneous coronary intervention (PCI), or whether to perform pharmacological treatment for the subject, or the like, with ease.

Figure 6B:
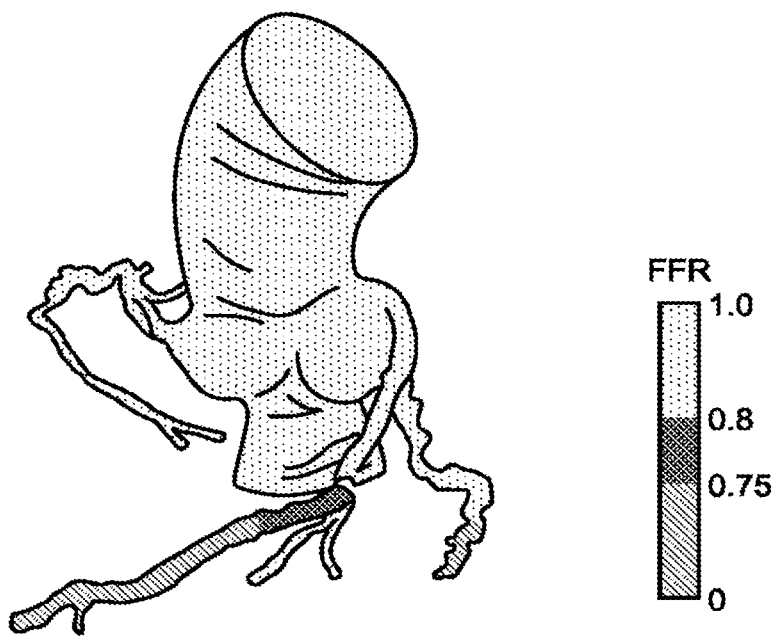
FIG. 6B shows one example of a color image that is generated by the generation function according to the first embodiment.

The reference value set by the generation function 354 can be set according to the switching information. That is, the number of reference values or a numeric value of the reference value can be set so as to change according to the switching information. For example, the number of reference values can be set according to information of a doctor in charge included in the examination information, information of the number of examinations included in the subject information, and the like. For example, in the case of having the examination for several times for follow-up, or the case of a predetermined doctor in charge determined in advance, the generation function 354 sets "0.8" and "0.75" as the reference values as shown in FIG. 6B, and generates three-color image in which the color changes at the set reference values "0.8" and "0.75" as boundaries. That is, the generation function 354 classifies values of FFR analyzed by the analysis function 352 for each position of a coronary artery of a subject into three regions of "lower than 0.75", "equal to or larger than 0.75 and smaller than 0.8", and "0.8 or larger". The generation function 354 then determines a color for each of the three regions, and generates a color image in which each position in a model image of a blood vessel of the subject is colored with the determined color.

Figure 6C:
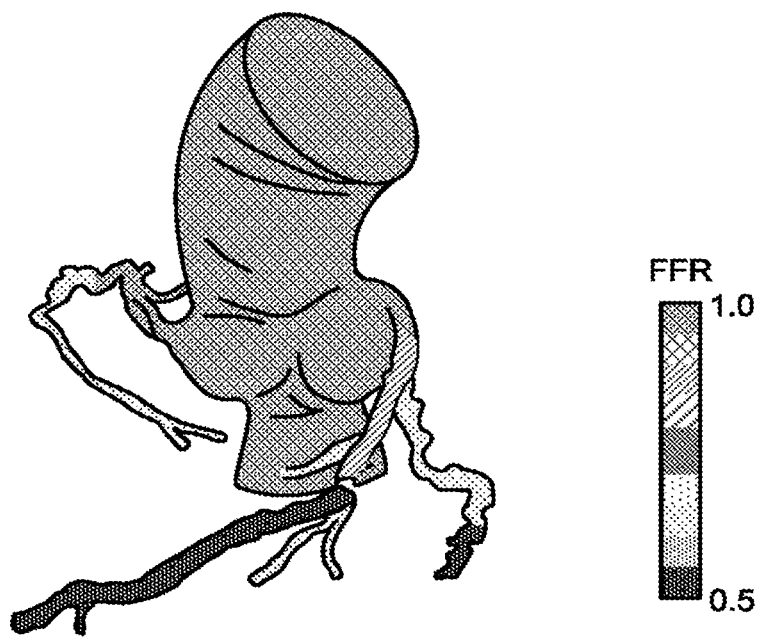
FIG. 6C shows one example of a color image that is generated by the generation function according to the first embodiment.

Moreover, in the case of the first examination, for example, the generation function 354 sets respective values obtained by dividing values from "0.5" to "1.0" into nine groups as the reference values as shown in FIG. 6C, and generates a nine-color image in which the color changes at the set respective reference values as boundaries. That is, the generation function 354 classifies values of FFR analyzed by the analysis function 352 for each position of a coronary artery of a subject into nine regions. The generation function 354 then determines a color for each of the nine regions, and generates a color image in which each position in a model image of a blood vessel of the subject is colored with the determined color.

A numeric value of the reference value set by the generation function 354 can be determined according to the switching information. For example, an example in which "0.8" and "0.75" are determined as the reference values has been shown in FIG. 6B, these values can be changed appropriately according to the information of the examination results of a subject, the body type information of a subject, and the like. For example, when the instantaneous FFR is used as the index value, the generation function 354 can determine "0.86" and "0.93" as the reference values. Furthermore, when the cardiac mass, the body weight, and the BMI of a subject are large, for example, the generation function 354 can set the two reference values "0.8" and "0.75" to higher values.

Moreover, the generation function 354 can determine the reference value based on various other kinds of switching information. For example, the generation function 354 set the reference value to relatively high values for a subject that has experienced a myocardial infarction, a subject having arrhythmia, a subject for which medicines such as an anti-platelet drug and an anticoagulant drug are prescribed, a subject having a high cholesterol level, and the like. Furthermore, the generation function 354 can change the reference value, for example, according to results of a medical checkup of each subject. Moreover, the generation function 354 can determine the reference value, for example according to the nationality, race, residential area, and belonging organization of a subject.

The ranges of an index value colored by the generation function 354 can also be set according to the switching information. For example, although the case in which the range of FFR to be colored is set to "0 to 1.0" is shown in FIG. 6A and FIG. 6B, it can be set to "0.5 to 1.0" according to the switching information as shown in FIG. 6C. As one example, when values of FFR are precisely checked, the generation function 354 can sets the range of FFR to be colored to a narrow range, and can generate a color image that is color-coded based on multiple reference values.

Furthermore, although the case of varying colors (tones) using the reference values as boundaries has been explained, colors used therefor can be determined so as to emphasize a region of interest. For example, the generation function 354 arranges a color such that the region in which a value of FFR is "smaller than 0.75" is prominent, or arranges colors such that the region of "smaller than 0.75" and the region of "0.75 and larger" are clearly distinguished from each other. That is, the generation function 354 generates a color image in which an index value included in a predetermined range based on the reference value is emphasized. Thus, an observer can recognize a position of a region of interest at a glance.

Moreover, the generation function 354 can vary the brightness or vary the transparency based on the reference value as a boundary also. Specifically, the generation function 354 sets the reference value for an index value according to the switching information, and generates a color image in which the brightness of color changes at the set reference value as a boundary. For example, the generation function 354 generates a color image in which the region of an FFR value being "smaller than 0.75" has high brightness. Furthermore, the generation function 354 sets the reference value for an index value according to the switching information, and generates a color image in which the transparency changes at the set reference value as a boundary. For example, the generation function 354 generates a color image in which the region of an FFR value being "0.75 and larger" has low transparency, and the region of an FFR value being "smaller than 0.75" has high transparency. As described, the generation function 354 can emphasize a region of interest in a color image by generating a color image in which the brightness or the transparency varies based on the reference value as a boundary.

Figure 6D:
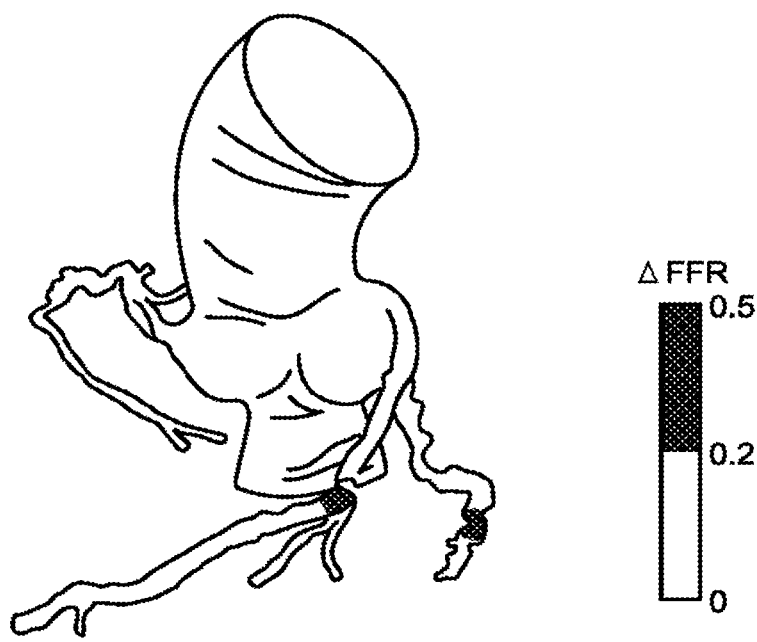
FIG. 6D shows one example of a color image that is generated by the generation function according to the first embodiment.

In the above example, the case of using the FFR as an index value has been explained. The generation function 354 can generate a color image using an index, such as ΔFFR, pressure, flow rate, and stenosis rate, other than the FFR. For example, the generation function 354 sets a reference value for ΔFFR, and generates a color image in which the color is varied based on the set reference value as a boundary as shown in FIG. 6D. As one example, the generation function 354 sets "0.2" as the reference value of ΔFFR, and generates a two-color image in which the color changes at the set reference value "0.2" as a boundary. That is, the generation function 354 classifies values of ΔFFR analyzed by the analysis function 352 for each position of a blood vessel of a subject into two ranges based on "0.2" as a boundary. The generation function 354 then determines a color of each of the two ranges (for example, red for values equal to or larger than 0.2 and white for values smaller than 0.2, or the like), and generates a color image in which each position in a model image of a blood vessel of the subject is colored with the determined color. Thus, an observer can recognize the region of a high ΔFFR value (that is, a portion at which the FFR changes significantly) at a glance.

The generation function 354 can generate various kinds of color images using pressure, flow rate, stenosis rate, or the like as an index, other than ΔFFR described above. The number of reference values or the numeric value of the reference value are set appropriately according to the switching information also for indexes such as ΔFFR, pressure, flow rate, and stenosis rate.

Figure 6E:
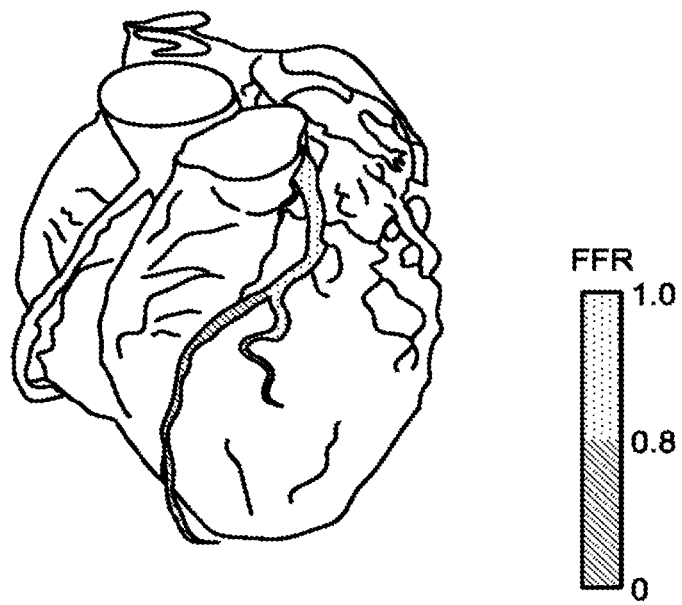
FIG. 6E shows one example of a color image that is generated by the generation function according to the first embodiment.

With FIG. 6A to FIG. 6D described above, the case of a color image in which colors are reflected in a model image of a blood vessel that has been generated based on a volume image of a subject has been explained. However, the embodiment is not limited thereto. The generation function 354 can generate a color image in which colors are reflected to various kinds of clinical images. For example, the generation function 354 sets "0.8" as the reference value of FFR as shown in FIG. 6E, and generates a two-color image in which the color changes at the set reference value "0.8" as a boundary, based on a volume rendering image. That is, the generation function 354 classifies values of FFR analyzed by the analysis function 352 for each position of a coronary artery of a subject into two ranges based on "0.8" as a boundary. The generation function 354 then determines a color of each of the two ranges, and generates a color image in which each position in the volume rendering image including the heart and blood vessels of the subject is colored with the determined color.

Figure 6F:
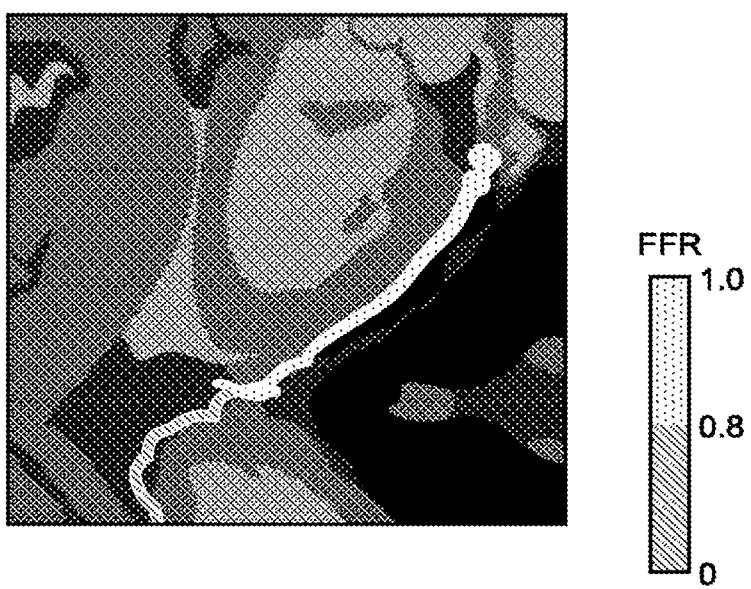
FIG. 6F shows one example of a color image that is generated by the generation function according to the first embodiment.

Moreover, for example, the generation function 354 sets "0.8" as the reference value of FFR as shown in FIG. 6F, and generates a two-color image in which the color changes at the set reference value "0.8" as a boundary, based on a CPR image. That is, the generation function 354 classifies values of FFR analyzed by the analysis function 352 for each position of a coronary artery of a subject into two ranges based on "0.8" as a boundary. The generation function 354 then determines a color of each of the two ranges, and generates a color image in which each position in the CPR image a blood vessel of the subject is colored with the determined color.

Figure 7A:
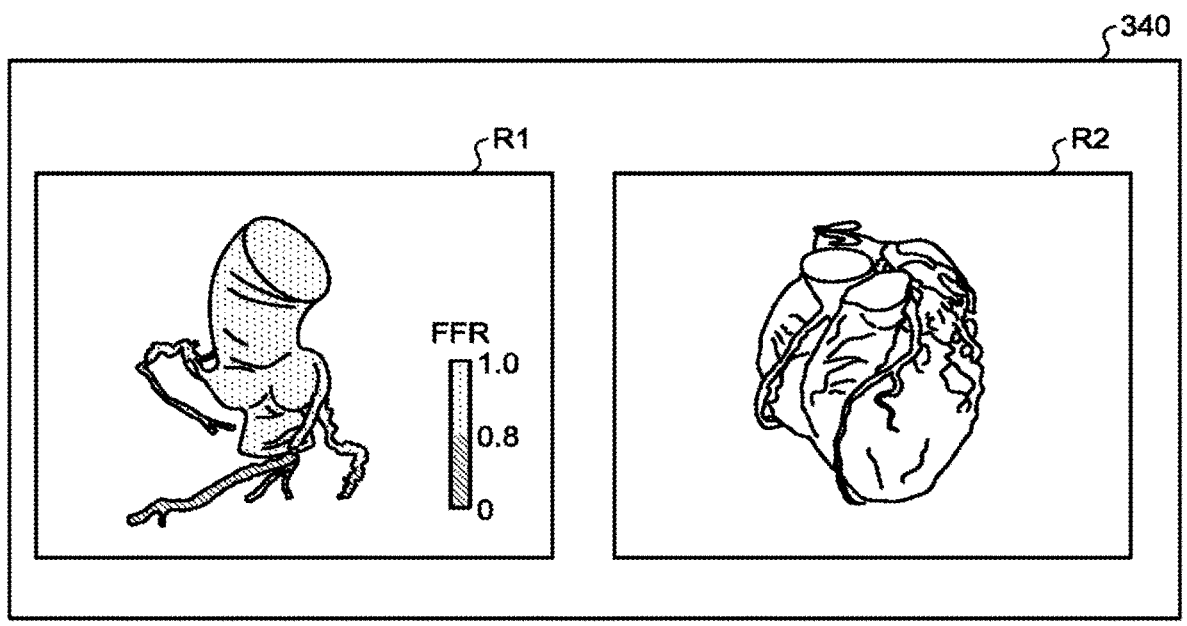
FIG. 7A shows one example of a color image that is generated by the generation function according to the first embodiment.
Figure 7B:
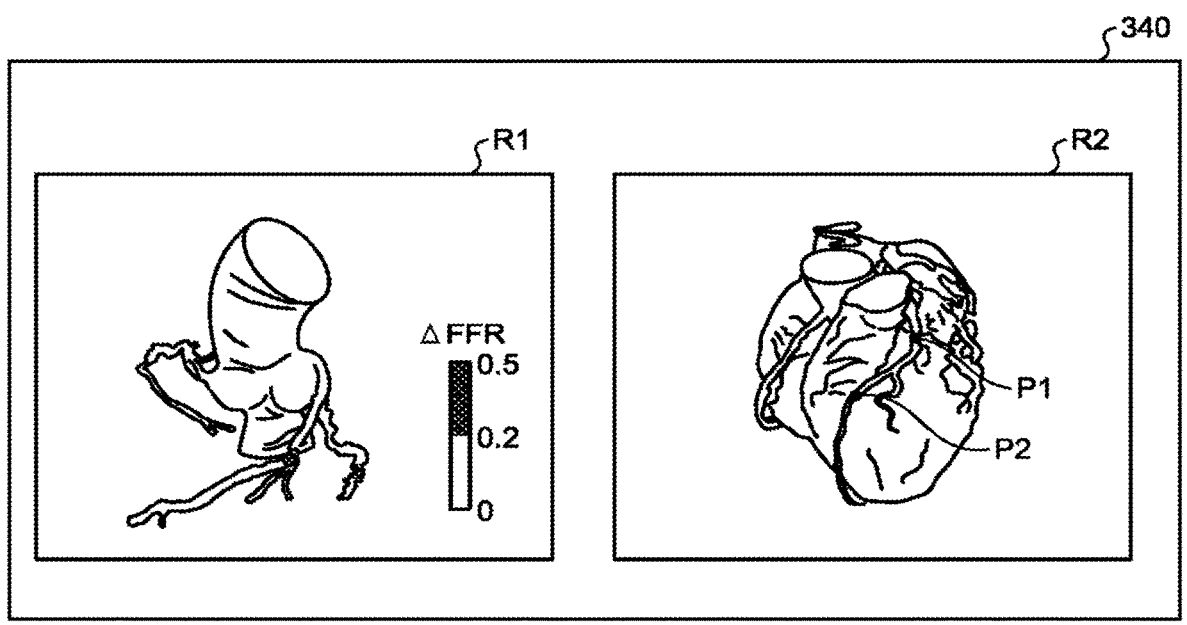
FIG. 7B shows one example of a color image that is generated by the generation function according to the first embodiment.
Figure 8A:
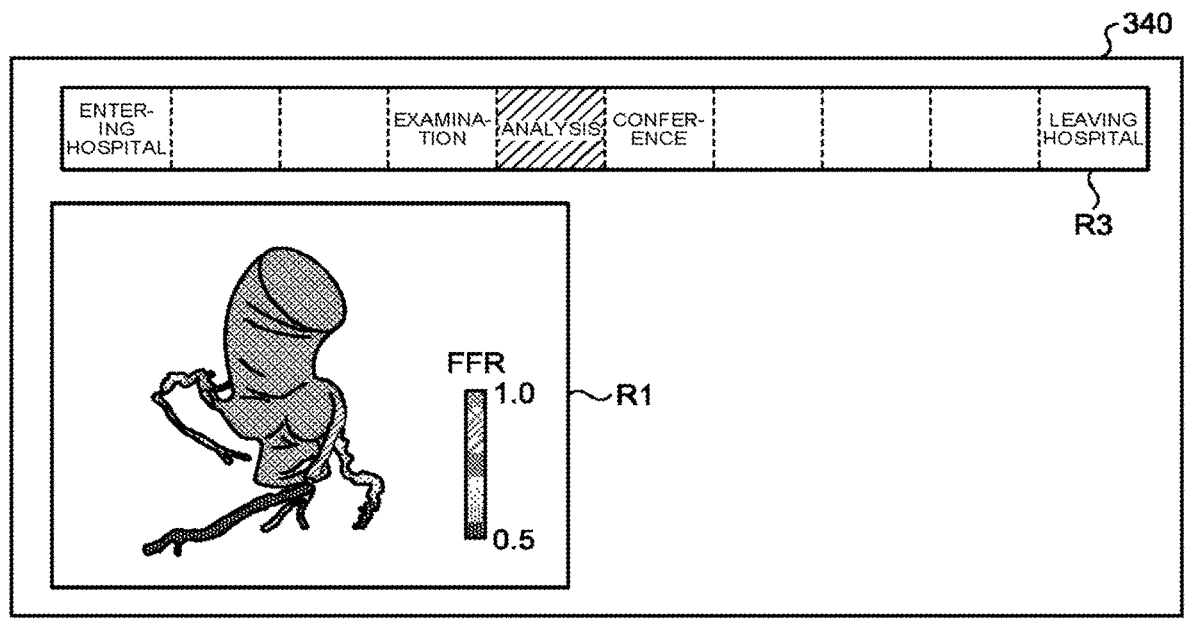
FIG. 8A shows one example of a color image that is generated by the generation function according to the first embodiment.
Figure 8B:
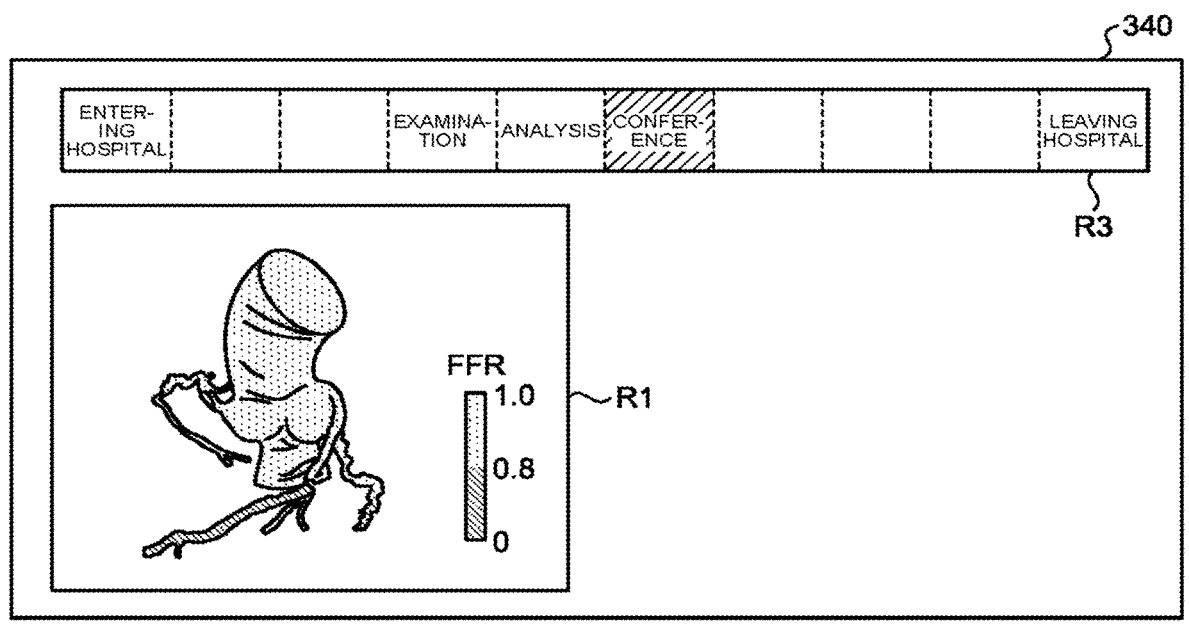
FIG. 8B shows one example of a color image that is generated by the generation function according to the first embodiment.
Figure 9A:
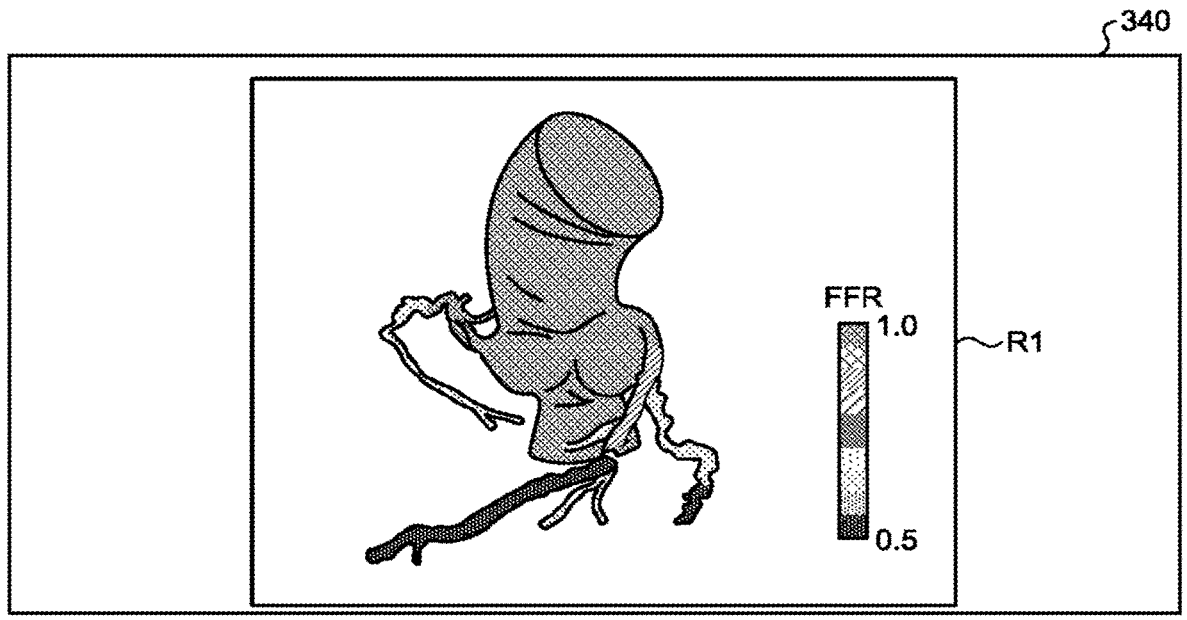
FIG. 9A shows one example of a color image that is generated by the generation function according to the first embodiment.
Figure 9B:
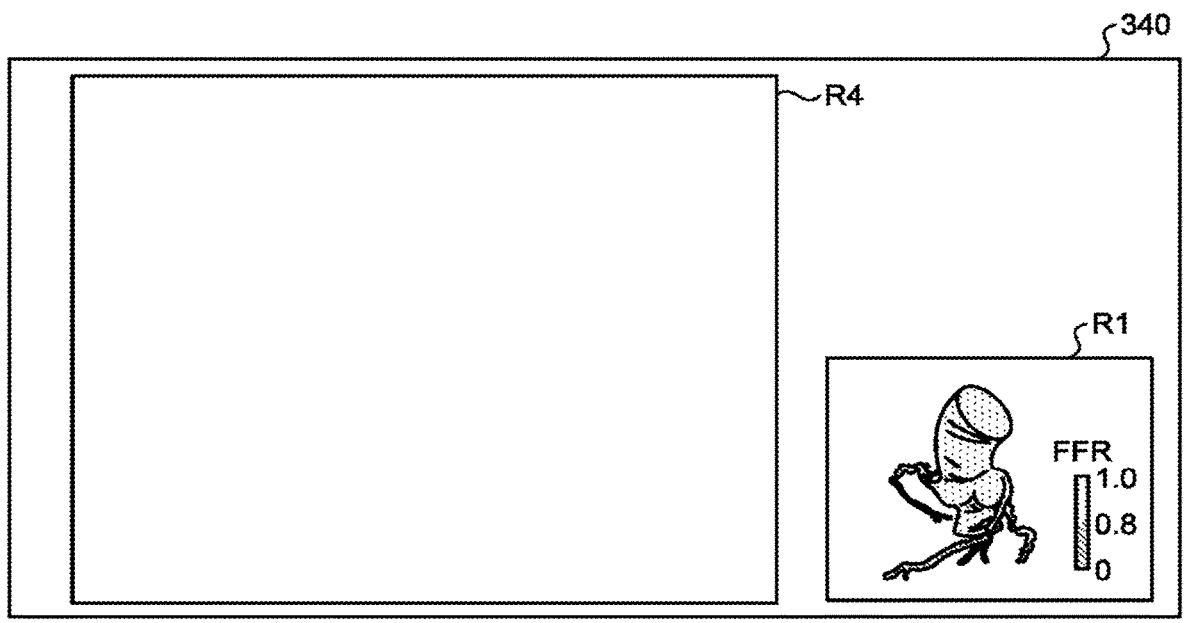
FIG. 9B shows one example of a color image that is generated by the generation function according to the first embodiment.

Furthermore, the generation function 354 can generate a color image according to the switching information of an image to be displayed along with an index value, information of an application to be used with the index value, a display purpose of the index value, a display region of the index value, and the like. FIG. 7A to FIG. 9B show one example of a color image that is generated by the generation function 354 according to the first embodiment. FIG. 7A and FIG. 7B show an example of a case of displaying an image along with an index value. Moreover, FIG. 8A and FIG. 8B show an example of a case of using information that indicates a display purpose of an index value. Furthermore, FIG. 9A and FIG. 9B show an example of a case of using a display region of an index value.

For example, the generation function 354 displays an index value in a display region R1 on the display 340 as shown in FIG. 7A, and generates, when displaying an image in a display region R2, a color image to be displayed in the display region R1 according to a type of an image to be displayed in a display region R2. As one example, when a volume rendering image of an entire heart including coronary arteries is displayed in the display region R2 as shown in FIG. 7A, the generation function 354 sets the reference value of FFR to "0.8", and generates a color image based on a two-color table in which the color changes at the set reference value "0.8" as a boundary. That is, the generation function 354 generates a color image with few colors (for example, two colors, or the like) enabling to determine a state of blood flow simply when an image showing an entire heart is displayed. For example, when an MPR image in which a coronary artery is enlarged, or the like is displayed in the display region R2, the generation function 354 sets respective values obtained by dividing values from "0.5" to "1.0" into nine groups as the reference values as shown in FIG. 6C, and generates a color image based on a nine-color table in which the color changes at the set respective reference values as boundaries. That is, the generation function 354 generates a color image with many colors (for example, nine colors, or the like) enabling to determine a state of blood flow more precisely when a detailed image is displayed. The generation function 354 can generate a color image according to other types of images, a part displayed in an image, or the like also.

Moreover, the generation function 354 can generate a color image according to various kinds of operations made with respect to a displayed image, not only according to a type of image displayed on the display 340. For example, when the acquisition function 353 accepts an operation of specifying a coronary artery region with respect to a volume rendering image of a heart shown in FIG. 7A through the input interface 330 the generation function 354 determines that it has been switched to a local image, and generates a nine-color image as a color image to be displayed in the display region R1.

Furthermore, for example, the acquisition function 353 accepts a position specifying operation with respect to a displayed image through the input interface, the generation function 354 generates a color image according to the operation accepted on the image. As one example, when the acquisition function 353 accepts an operation of specifying a portion a position P1 to a position P2 along a blood vessel on a coronary artery in a volume rendering image as shown in FIG. 7B, the generation function 354 generates a color image showing ΔFFR from the position P1 to the position P2 specified. Moreover, when the acquisition function 353 accepts an operation of specifying two points of the position P1 and the position P2, the generation function 354 generates a color image showing a difference (ΔFFR) between an FFR value at the specified position P1 and an FFR value at the position P2. As described, the generation function 354 can generate a color image according to a type of an image that is displayed along with an index value, or to an operation with respect to an image. When generating a color image according to a position specified on an image (for example, a color image showing ΔFFR) is generated, an image displayed in the display region R2 is an image generated based on medical image data obtained by analyzing an index value.

Furthermore, the generation function 354 generates a color image according to information relating to a display purpose of an index value acquired by the acquisition function 353. The acquisition function 353 acquires information relating to a display purpose of an index value based on an operation in various kinds of applications. For example, a management application that manages subject information chronologically, and enables to browse various kinds of examination information has been used in recent years. The acquisition function 353 acquires the switching information relating to a display purpose of an index value from an operation in this kind of management application. As one example, the acquisition function 353 acquires a display purpose of an index value from information of operation in an application that manages various kinds of information about a subject from entering to leaving of a hospital, and that presents the information to a user as shown in a region R3 of FIG. 8A and FIG. 8B.

For example, when a display operation of an index value using various kinds of information of a subject shown chronologically is performed, the acquisition function 353 acquires a display purpose of the index value based on the performed operation. For example, as shown in FIG. 8A, when a user selects "analysis" from among various kinds of information of the subject shown chronologically as a display operation to display an index value, the acquisition function 353 acquires "analysis" as the information indicating a display purpose of the index value. That is, the acquisition function 353 acquires the above display operation as information indicating that the index value to perform analysis is displayed. When the acquisition function 353 accepts the operation of selecting "analysis", the generation function 354 generates a color image with many colors (for example, nine colors, or the like) enabling to determine a state of blood flow precisely, which is suitable for analysis of blood flow, as shown in FIG. 8A.

On the other hand, when a user selects "conference" from among the various kinds of information of the subject shown chronologically as a display operation to display an index value as shown in FIG. 8B, the acquisition function 353 acquires "conference" as the information indicating a display purpose of the index. That is, the acquisition function 353 acquires the above display operation as information indicating that the index value to be used in a conference is displayed. As cases of multiple people are observed at a conference, color images that enables diagnosis simply are often displayed. Therefore, when the acquisition function 353 accepts an operation of selecting "conference", the generation function 354 generates a color image with few colors (for example, two colors, or the like) enabling to determine a state of blood flow simply, which is suitable for analysis of blood flow.

Because various kinds of applications are often activated for one subject at a conference, this information can be used as the switching information. For example, when the acquisition function 353 determines the number of applications activated at the same time, and when the number of applications equal to or more than a threshold are activated, it can be configured to determine that the display purpose is "conference".

Moreover, the generation function 354 can generate a color image based on a display region of a color image on the display 340 also. Specifically, the generation function 354 generates a color image according to a size of the display region, a position of the display region, or the like of a color image. For example, when the display region R1 on the display 340 is large as shown in FIG. 9A, the generation function 354 generates a color image with many colors (for example, nine colors) enabling to determine a state of blood flow precisely, which is suitable for analysis of blood flow. Furthermore, when the display region R1 is arranged at a center of the display 340, or when the display region R1 is the entire screen, the generation function 354 generates a color image with many colors (for example, nine colors) enabling to determine a state of blood flow precisely, which is suitable for analysis of blood flow.

On the other hand, when the display region R1 on the display 340 is small, or when a display region R4 to display something other than a color image is arranged in addition thereto as shown in FIG. 9B, the generation function 354 generates a color image with few colors (for example, two colors) enabling to determine a state of blood flow simply. Moreover, when the display region R1 is arranged at an end portion of a display 430, the generation function 354 generates a color image of few colors (for example, two colors) enabling to determine a state of blood flow simply.

As described above, the generation function 354 generates a color image according to the information of a display purpose of an index value. For the information relating to a display purpose, not only the example described above, but also various other kinds of information can be used. For example, the display purpose can be determined using a display time of a color image. In this case, for example, the acquisition function 353 acquires a display time of a color image. Subsequently, when the display time of the color image exceeds a threshold (for example, 10 minutes), the generation function 354 generates a color image with many colors (for example, nine colors) enabling to determine a state of blood flow precisely, which is suitable for analysis of blood flow. On the other hand, when the display time of the color image is equal to or shorter than the threshold (for example, 1 minute), the generation function 354 generates a color image with few colors (for example, two colors) enabling to determine a state of blood flow simply. It can be configured to generate a color image with many colors (or a color image with few colors) when color images exceeding the threshold (or equal to or shorter than the threshold) continues.

Furthermore, it can be controlled to switch color images according to the display time, for example. In this case, for example, the generation function 354 first generates a color image with few colors. The acquisition function 353 then acquires the display time of the color image with few colors. When the display time of the color image with few colors exceeds the threshold, the generation function 354 generates a color image with many colors. That is, the generation function 354 determines how deeply the color image is observed, and controls to generate a detailed color image when determining that it has been observed for a long time.

Moreover, it can be controlled to change a color image to be generated according to how many times the observation has been done. For example, when an index value is saved, it can be associated with information indicating that the analysis has been done. The acquisition function 353 acquires information indicating whether an index value used at generating a color image is associated with the information indicating that analysis has been done, as the switching information. When the information indicating that analysis has been done is associated with the index value, the generation function 354 generates a color image with few colors (for example, two colors) enabling to determine a state of blood flow simply. On the other hand, when the information indicating that analysis has been done is not associated with the index value (when it is the first analysis), the generation function 354 generates a color image with many colors (for example, nine colors) enabling to determine a state of blood flow precisely.

As described above, the generation function 354 generates a color image in which index values are colored in a display mode according to the switching information. To the switching information used by the generation function 354, order of priority can be determined. For example, when the acquisition function 353 informs multiple kinds of the switching information to the generation function 354, the order of priority to determine which switching information is to be used to decide a display mode of a color image by the generation function 354 can be determined. As one example, for "urgent" in the examination information and "first examination" in the subject information, the order of priority can be determined such that a priority is given to "urgent". In this case, when "urgent" and "first examination" are informed by the acquisition function 353 as the switching information, the generation function 354 generates a two-color image giving priority to "urgent".

Referring back to FIG. 2, the display control function 355 causes the display 340 to display a color image. Specifically, the display control function 355 causes the display 340 to display a color image that has been generated by the generation function 354. The display control function 355 switches color images to be displayed according to a switching operation for color images. For example, when the switching information is input through the input interface 330 after displaying a color image generated by the generation function 354 on the display 340, the display control function 355 switches to a color image that is generated based on the switching information input from the input interface 330 from a color image that has been displayed.

As one example, suppose the generation function 354 generates a color image in which FFR values are reflected, and the display control function 355 causes the display 340 to display the generated color image. When the input interface 330 accepts an input of ΔFFR as the switching information in this situation, the generation function 354 first generates a color image in which values of ΔFFR are reflected. Subsequently, the display control function 355 causes the display 340 to display the color image of ΔFFR newly generated.

As described, the medical image-processing apparatus 300 can switch color images to be displayed based on the switching information that is received from an operator through the input interface 330. The switching information that is input by an operator through the input interface 330 includes information of the number of reference values and a numeric value, and the like, in addition to the index type information, the examination information, and the subject information described above. That is, the operator can perform selection of index type, input of the examination information or the subject information, and setting of the number of reference values (the number of colors used in a color image) or a numeric value thereof at arbitrary timing.

Next, a procedure of processing performed by the medical image-processing apparatus 300 according to the first embodiment is explained. FIG. 10 is a flowchart showing a procedure of processing performed by the medical image-processing apparatus 300 according to the first embodiment. Step S101 and step S102 in FIG. 10 are implemented, for example, by calling a program corresponding to the analysis function 352 from the memory 320 and executing it by the processing circuitry 350. Moreover, step S103 is implemented, for example, by calling a program corresponding to the acquisition function 353 from the memory 320 and executing it by the processing circuitry 350. Furthermore, step S104 and step S105 are implemented by calling a program corresponding to the generation function 354 from the memory 320 and executing it by the processing circuitry 350. Moreover, step S106 is implemented by calling a program corresponding to the display control function 355 from the memory 320 and executing it by the processing circuitry 350.

In the medical image-processing apparatus 300 according to the present embodiment, the processing circuitry 350 first performs the fluid analysis using collected CT image data (step S101), and calculates an index value (for example, FFR) relating to blood flow (step S102). Subsequently, the processing circuitry 350 acquires external information (step S103), and determines the display mode based on the external information (step S104).

The processing circuitry 350 then generates a color image based on the determined display mode (step S105), and displays the generated color image (step S106).

As described above, according to the first embodiment, the analysis function 352 performs fluid analysis of an image that includes a blood vessel of a subject, to acquire an index value relating to blood flow at each position of the blood vessel. The acquisition function 353 acquires the switching information to switch the display mode at displaying the index value. The generation function 354 generates a color image in which the index value is reflected in the display mode according to the switching information for an image showing the blood vessel of the subject. The display control function 355 causes a display unit to display the color image. Therefore, the medical image-processing apparatus 300 according to the first embodiment can generate and display a color image in a display mode according to the switching information, and enables to display a color image that facilitates observation of an index relating to blood flow.

Furthermore, according to the first embodiment, the acquisition function 353 acquires at least one of the index type information, the examination information, and the subject information, as the switching information. The generation function 354 generates a color image in which the index value is reflected in a display mode according to at least one of the index type information, the examination information, and the subject information. Therefore, the medical image-processing apparatus 300 according to the first embodiment enables to generate and display a color image according to various kinds of situations flexibly.

Moreover, according to the first embodiment, the generation function 354 sets a reference value for an index value according to the switching information, and generates a color image in which the color changes at the set reference value as a boundary. Therefore, the medical image-processing apparatus 300 according to the first embodiment enables to generate and display a color image suitable for diagnosis according to a situation.

Furthermore, according to the first embodiment, the generation function 354 sets a reference value for an index value according to the switching information, and generates a color image in which the brightness of color changes at the set reference value as a boundary. Furthermore, the generation function 354 sets a reference value for an index value according to the switching information, and generates a color image in which the transparency changes at the set reference value as a boundary. Moreover, the generation function 354 generates a color image in which index values within a predetermined range based on the reference value are emphasized. Therefore, the medical image-processing apparatus 300 according to the first embodiment enables to generate and display a color image in which a region of interest is emphasized, and to display a color image that facilitates observation of an index relating to blood flow.

Furthermore, according to the first embodiment, the generation function 354 sets a reference value for each type of index value. Therefore, the medical image-processing apparatus 300 according to the first embodiment can generate and display a color image that is suitable for diagnosis per type of index value, and enables to display a color image that facilitates observation of an index relating to blood flow.

Moreover, according to the first embodiment, the generation function 354 generates a color image that expresses an internal portion of a blood vessel in an image showing the blood vessel of a subject with colors corresponding to index values relating to blood flow at each position. Therefore, the medical image-processing apparatus 300 according to the first embodiment can generate and display a color image for which differences in color of the color image can be easily determined, and enables to display a color image that facilitates observation of an index relating to blood flow.

Second Embodiment

In the above first embodiment, the case of generating a color image in which an entire internal portion of a blood vessel is colored has been explained. In a second embodiment, a case of displaying display information in which an index value at each position of a blood vessel is expressed with a color along the blood vessel is explained. The configuration of the medical image-processing apparatus 300 according to the second embodiment is basically the same as the configuration of the medical image-processing apparatus 300 shown in FIG. 2. Therefore, points that differ from the medical image-processing apparatus 300 according to the first embodiment are mainly explained in the following, and the same reference symbols are assigned to components taking similar roles as those of the components shown in FIG. 2, and details explanation thereof is omitted.

The generation function 354 according to the second embodiment generates a color image in which a line along a blood vessel in an image showing the blood vessel of a subject is expressed by a color corresponding to an index value relating to blood flow at each position in a direction of length of the blood vessel. That is, the generation function 354 generates a color image in which a line along a blood vessel is colored, not an entire internal portion of the blood vessel.

Figure 11:
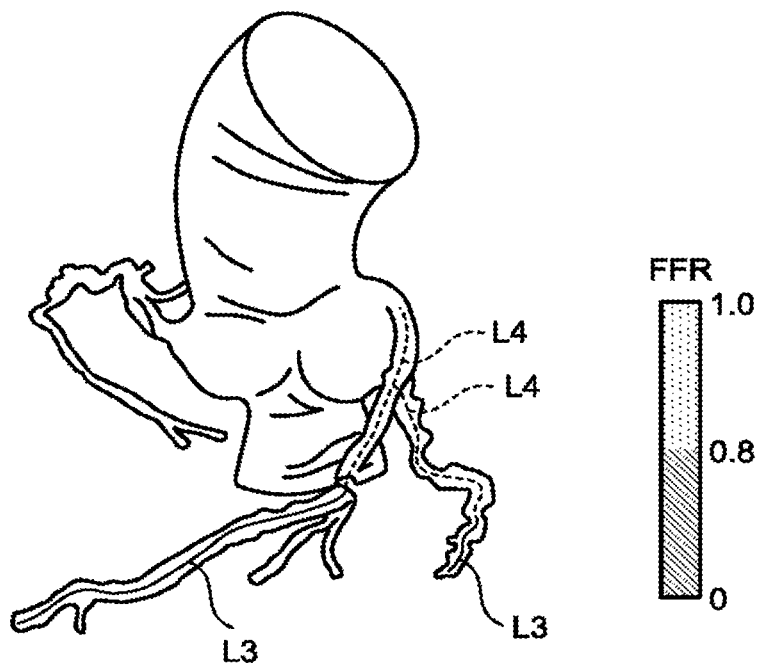
FIG. 11 shows one example of a color image that is generated by a generation function according to a second embodiment.

FIG. 11 shows one example of a color image that is generated by the generation function 354 according to the second embodiment. FIG. 11 shows an example of a color image in which a model image of a blood vessel of a subject is colored in two colors. For example, the generation function 354 generates a color image in which a center line of a blood vessel is indicated in a model image, and each center line is colored with a color according to a value of an index value as shown in FIG. 11. As one example, the generation function 354 sets a reference value to "0.8", and generates a color image a center line of a blood vessel is colored based on a value of FFR at each position in the direction length of a coronary artery as shown in FIG. 11. That is, the generation function 354 generates a color image in which a curved line L3 along a portion at which the value of FFR is "smaller than 0.8" is colored with a color corresponding to "smaller than 0.8", and a curved line L4 along a portion at which the value of FFR is "0.8 or larger" is colored with a color corresponding to "0.8 or larger" as shown in FIG. 11.

For example, a region in which blood vessels run complicatedly can be difficult to see where the blood vessels run if the entire internal portion of each blood vessel is colored. Therefore, the medical image-processing apparatus 300 according to the second embodiment colors only a line along a blood vessel as shown in FIG. 11, thereby enabling to grasp where the blood vessels run easily, and to display a color image that facilitates observation of an index relating to blood flow.

Figure 12A:
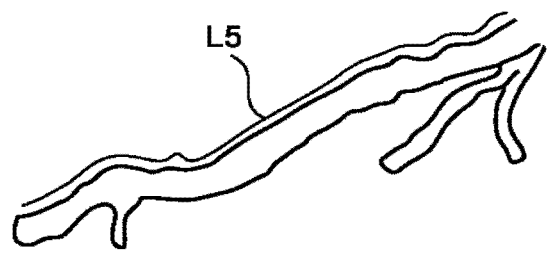
FIG. 12A shows a generation example of a color image that is generated by the generation function according to the second embodiment.
Figure 12B:
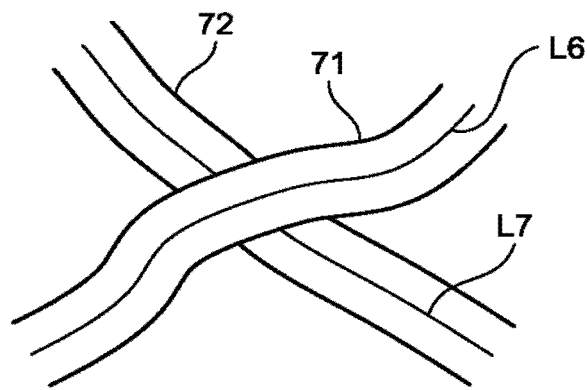
FIG. 12B shows a generation example of a color image that is generated by the generation function according to the second embodiment.
Figure 12C:
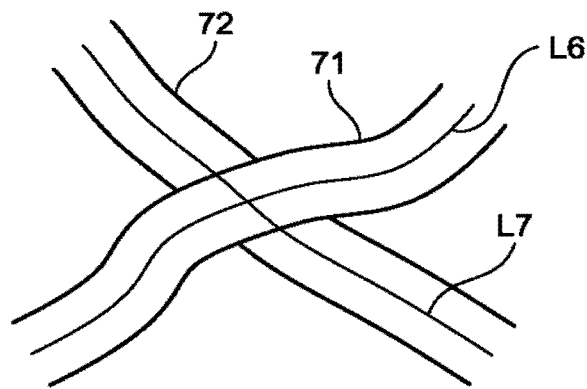
FIG. 12C shows a generation example of a color image that is generated by the generation function according to the second embodiment.

Note that the example shown in FIG. 11 is just one example, and the generation function 354 can generate various other kinds of color images. FIG. 12A to FIG. 12C show one example of a color image that is generated by the generation function 354 according to the second embodiment. In FIG. 12A to FIG. 12C, only one region in a color image is shown.

For example, the generation function 354 shows a line L5 along a blood vessel on the outside of the blood vessel as shown in FIG. 12A, and can generate a color image in which the line L5 is expressed by a color according to a value of the index value. That is, the generation function 354 can generate a color image in which color information is shown on the outside of the blood vessel also, not just coloring the internal portion of the blood vessel.

The line indicating an index value on the outside of a blood vessel can be arranged to indicate a difference in an index value not only by color but also by thickness of the line. As one example, the generation function 354 can display a line along a portion in which the value of FFR is "smaller than 0.75" in a coronary artery thicker than a line along a portion of "0.75 or larger". Moreover, the generation function 354 can generate, for example, an image in which the number of dots according to an index value are arranged in a direction perpendicular to a direction length of a blood vessel. As one example, the generation function 354 generates an image in which the number of dots arranged beside a blood vessel increases as the value of FFR decreases.

Furthermore, the generation function 354 can display lines in various forms in a region in which blood vessels intersect. For example, as shown in FIG. 12B, when a blood vessel 71 and a blood vessel 72 intersect, and the blood vessel 71 comes in front of the blood vessel 72, the generation function 354 can generate a color image in which a line L6 along the blood vessel 71 is displayed above a lone L7 along the blood vessel 72 so as to show the positional relationship of the blood vessels accurately. Moreover, the generation function 354 can generate a color image in which an entire part of the line L7 is displayed as shown in FIG. 12C to show the entire part of the line L7 that is partially hidden by the blood vessel 71.

As described above, according to the second embodiment, the generation function 354 generates a color image in which a line along a blood vessel in an image showing the blood vessel of a subject is displayed with a color corresponding to an index value relating to blood flow at each position in the direction of length of the blood vessel. Therefore, the medical image-processing apparatus 300 according to the second embodiment enables to display a color image that facilitates observation of an index relating to blood flow, while enabling easy grasping of arrangement of blood vessels.

Third Embodiment

The first and the second embodiments have been explained. In addition to the first and the second embodiments described above, various different embodiments are possible.

In the embodiments described above, the case of displaying the FFR or the ΔFFR as an index relating to blood flow has been explained as an example. However, the embodiments are not limited thereto and, for example, a color image relating to another index, such as flow rate, flow speed, and pressure, can be displayed.

Furthermore, in the above embodiments, the case of using a single color table in which the color changes at a reference value as a boundary has been explained. However, the embodiments are not limited thereto, and a color table to be applied can be changed according to a position of an index value indicating the same value as the reference value on a blood vessel. Specifically, the acquisition function 353 acquires a position indicating the same value as the reference value of the index value on a blood vessel as for the index value relating to blood vessel at each position of the blood vessel, as the switching information. The generation function 354 then generates a color image in which arrangement of colors is changed according to the position of the index value indicating the same value as the reference value of the index value on the blood vessel out of the index values at the respective positions of the blood vessel.

For example, the acquisition function 353 acquires a position at which the index value is the same value as the reference value of the index value on the blood vessel as for the index value relating to blood flow at each position of the blood vessel based on an analysis result obtained by the analysis function 352. As on example, the acquisition function 353 acquires a position (for example, a distance from a starting portion) on a blood vessel at which the value of FFR is "0.7". That is, the acquisition function 353 acquires a position on the blood vessel at which the value of FFR is "0.7" from an analysis result of the vessel shape data and the FFR.

The generation function 354 changes a color table according to the position acquired by the acquisition function 353. The color tables used by the generation function 354 as appropriate have different color arrangement, for example, according to the seriousness. For example, in a color table in which a color indicating that the level of seriousness is high is used, multiple colors assigned based on the reference value as a boundary are colors in the red range. On the other hand, in a normal color table, various color tones, such as red, yellow, green, and blue, are assigned. For example, when a distance to a position at which the value of FFR is "0.7" from a starting portion is smaller than a threshold (when close to the starting portion), the generation function 354 generates a color image using the color table that uses colors indicating that the level of seriousness is high. On the other hand, when a distance to a position at which the value of FFR is "0.7" from a starting portion exceeds the threshold (when far from the starting portion), the generation function 354 generates a color image using the normal color table.

That is, when a position at which the value of FFR is "0.7" is close to the starting portion, a region (perfusion area) dominated by blood vessels at which the value of FFR is lower than "0.7" is large, and therefore, the level of seriousness is high. However, when a position at which the value of FFR is "0.7" is far from the starting portion, a region (perfusion area) dominated by blood vessels at which the value of FFR is lower than "0.7" is small, and therefore, the level of seriousness is less high. AS described above, the generation function 354 can generate a color image in which the difference in seriousness is reflected by changing the color tables according to a position that is acquired by the acquisition function 353. Although the case in which the color tables are changed according to a distance from a starting portion has been explained in the above example, the embodiments are not limited thereto. For example, the color tables can be changed according to a perfusion area.

Moreover, as for a correspondence between the switching information indicating a display condition of an index value explained in the embodiments and the display mode (setting of a reference value, color arrangement, and the like) of a color image, predetermined correspondences can be stored in the memory 320 in advance to be read as necessary by the generation function 354, but also a correspondence relationship that is updated as necessary by machine learning can be used.

Figure 13:
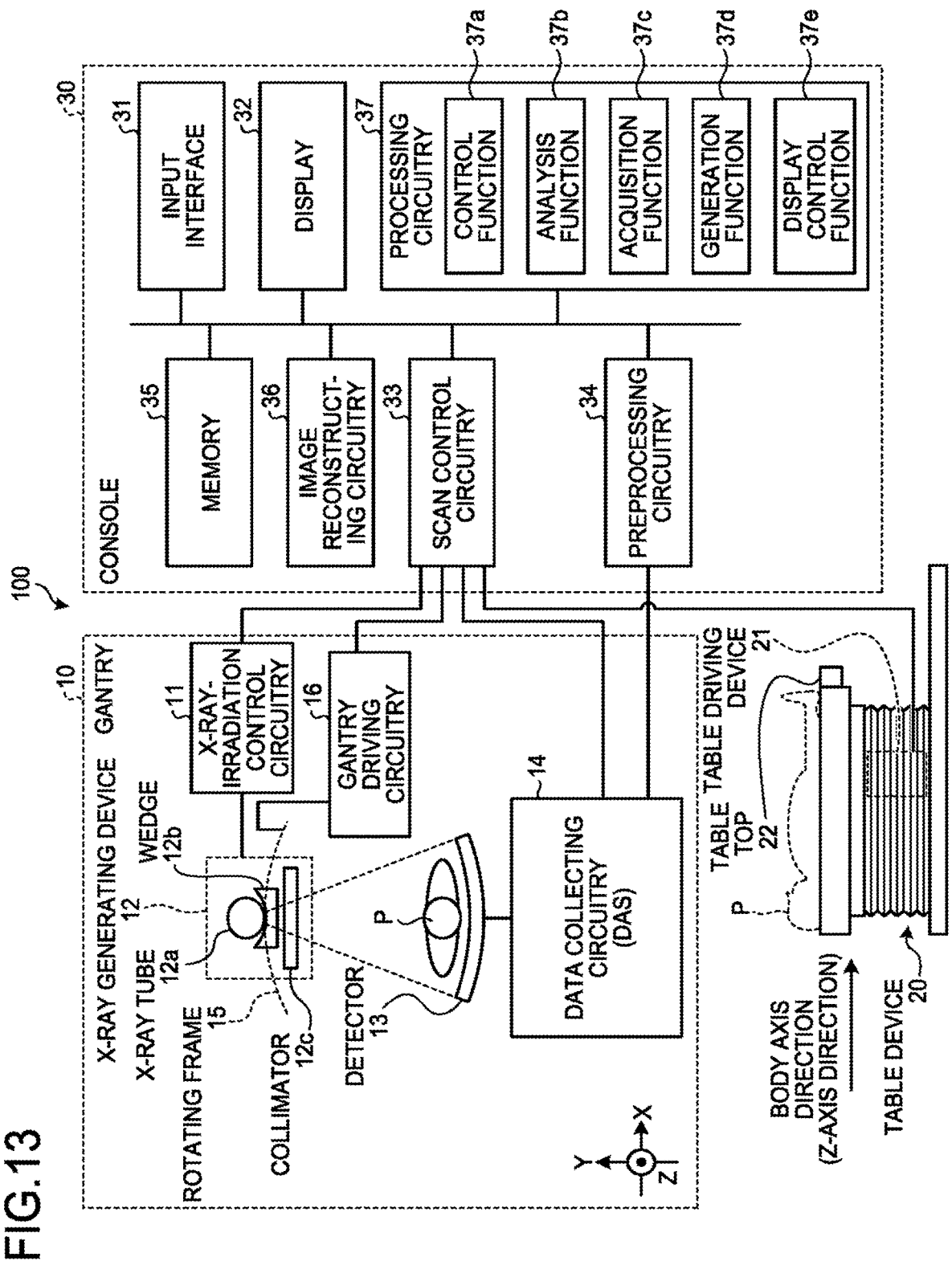
FIG. 13 shows one example of a configuration of an X-ray CT apparatus according to a third embodiment.

Furthermore, in the above embodiments, the case in which the medical image-processing apparatus 300 performs various kinds of processing has been explained. However, the embodiments are not limited thereto. For example, various kinds of processing can be performed by the X-ray CT apparatus 100. FIG. 13 shows one example of a configuration of the X-ray CT apparatus according to a third embodiment.

As shown in FIG. 13, the X-ray CT apparatus 100 according to the third embodiment includes a gantry 10, a table device 20, and a console 30. The gantry 10 is a device that irradiates an X-ray to a subject P, and detects an X-ray that has passed through the subject P to output to the console 30, and includes X-ray-irradiation control circuitry 11, an X-ray generating device 12, a detector 13, data collecting circuitry (data acquisition system (DAS)) 14, a rotating frame 15, and gantry driving circuitry 16.

The rotating frame 15 is an annular-shaped frame that supports the X-ray generating device 12 and the detector 13 so as to oppose to each other about the subject P, and that rotates at high speed in a circular orbit about the subject P in center by the gantry driving circuitry 16 described later.

The X-ray-irradiation control circuitry 11 is a device that supplies a high voltage to an X-ray tube 12a as a high-voltage generating unit, and the X-ray tube 12a generates an X-ray by using the high voltage supplied from the X-ray-irradiation control circuitry 11. The X-ray-irradiation control circuitry 11 adjusts an amount of X-ray to be irradiated to the subject P by adjusting a tube voltage and a tube current to be supplied to the X-ray tube 12a under control of scan control circuitry 33 described later.

Moreover, the X-ray-irradiation control circuitry 11 switches a wedge 12b. Furthermore, the X-ray-irradiation control circuitry 11 adjusts an irradiation range (a fan angle or a cone angle) of an X-ray by adjusting an opening degree of a collimator 12c. Note that in the present embodiment, it can be arranged such that more than one kind of wedge 12b is manually switched by an operator.

The X-ray generating device 12 is a device that generates an X-ray and irradiates the generated X-ray to the subject P, and includes the X-ray tube 12a, the wedge 12b, and the collimator 12c.

The X-ray tube 12a is a vacuum tube that irradiates an X-ray beam to the subject P by a high voltage supplied under control of the X-ray-irradiation control circuitry 11, and irradiates the X-ray beam onto the subject P with rotation of the rotating frame 15. The X-ray tube 12a generates an X-ray beam that radiates in a fan angle and a cone angle. For example, the X-ray tube 12a can emit an X-ray continuously all around the subject P for full reconstruction, or can emit an X-ray continuously in an irradiation range (180 degrees+ fan angle) enabling half reconstruction for the half reconstruction by the control of the X-ray-irradiation control circuitry 11. Moreover, the X-ray tube 12a can emit an X-ray intermittently (pulsed X-ray) at a predetermined position (tube position) by the control of the X-ray-irradiation control circuitry 11. Furthermore, the X-ray-irradiation control circuitry 11 can modulate the intensity of an X-ray to be emitted from the X-ray tube 12a also. For example, the X-ray-irradiation control circuitry 11 increases the intensity of an X-ray to be emitted from the X-ray tube 12a at a specific tube position, and decreases the intensity of an X-ray to be emitted from the X-ray tube 12a in a range other than the specific tube position.

The wedge 12b is an X-ray filter to adjust an amount of an X-ray that is emitted from the X-ray tube 12a. Specifically, the wedge 12b is a filter through which an X-ray irradiated from the X-ray tube 12a passes to be attenuated so that the X-ray to be irradiated to the subject P from the X-ray tube 12a has a predetermined distribution. For example, the wedge 12b is a filter that is obtained by processing aluminum to have a predetermined target angle and a predetermined thickness. The wedge is called wedge filter, or bow-tie filter.

The collimator 12c is a slit to narrow an irradiation range of an X-ray, the amount of which has been adjusted by the wedge 12b, by the control of the X-ray-irradiation control circuitry 11.

The gantry driving circuitry 16 rotates the X-ray generating device 12 and the detector 13 on a circular orbit about the subject P in center, by driving the rotating frame 15 to be rotated.

The detector 13 is a two-dimensional array detector (surface detector) that detects an X-ray that has passed through the subject P, and has rows of detecting devices in which X-ray detectors for multiple channels are arranged aligned along a Z-axis direction. Specifically, the detector 13 has X-ray detecting devices that are arranged in multiple rows of 320 rows along the Z-axis direction, and is capable of, for example, detecting an X-ray that has passed through the subject P in a wide range, such as a range including a lung and the heart of the subject P. The Z-axis direction indicates a direction of rotation center axis of the rotating frame 15 in a state in which the gantry 10 is not tilted.

The data collecting circuitry 14 is a DAS, and collects projection data from detection data of an X-ray detected by the detector 13. For example, the data collecting circuitry 14 performs amplification processing, analog-to-digital (A/D) conversion processing, sensitivity correction processing among channels, and the like on an X-ray-intensity distribution data that is detected by the detector 13, to generate projection data, and transmits the generated projection data to the console 30 described later. For example, when an X-ray is continuously emitted from the X-ray tube 12a while the rotating frame 15 is rotating, the data collecting circuitry 14 collects a projection data group corresponding to all circumference (360 degrees). Moreover, the data collecting circuitry 14 transmits the respective collected projection data associating with a tube position, to the console 30 described later. The tube position is information indicating a projection direction of the projection data. Note that the sensitivity correction processing among channels can be performed by preprocessing circuitry 34 described later.

The table device 20 is a device on which the subject P is placed, and as shown in FIG. 13, includes a table driving device 21, and a table top 22. The table driving device 21 moves the table top 22 in the Z-axis direction, and moves the subject P to the inside of the rotating frame 15. The table top 22 is a plate on which the subject P is placed. Although it has been explained that a change in a relative position of the gantry 10 and the table top 22 is achieved by controlling the table top 22 in the present embodiment, the embodiments are not limited thereto. For example, when the gantry 10 is self-propelled, the change in the relative position of the gantry 10 and the table top 22 can be achieved by controlling movement of the gantry 10.

The gantry 10 rotates the rotating frame 15 while moving the table top 22, for example, and performs helical scanning in which the subject P is scanned helically. Alternatively, the gantry 10 performs conventional scanning in which the subject P is scanned in a circular orbit by rotating the rotating frame 15 while the position of the subject P is fixed after the table top 22 is moved. Alternatively, the gantry 10 performs step-and-shoot in which the conventional scanning is performed in more than one scanning area while changing the position of the table top 22 at regular intervals.

The console 30 is a device that accepts an operation of the X-ray CT apparatus 100 by an operator, and that reconstructs X-ray-CT image data by using projection data collected by the gantry 10. The console 30 includes, as shown in FIG. 13, an input interface 31, a display 32, the scan control circuitry 33, the preprocessing circuitry 34, a memory 35, image reconstructing circuitry 36, and processing circuitry 37.

The input interface 31 is implemented by a mouse, a keyboard, a trackball, a switch, a button, a joystick, a touch pad in which an input operation is made by touching an operating surface, a touch screen in which a display screen and a touch pad are integrated, a non-contact input interface using an optical sensor, a voice input interface, and the like used by an operator of the X-ray CT apparatus 100 to input various kinds of instructions and settings. The input interface 31 is connected to the processing circuitry 37, and converts a received input operation into an electrical signal to output to the processing circuitry 37. The input interface 31 in the present application is not limited to one having physical operating parts, such as a mouse and a keyboard. For example, processing circuitry that receives an electrical signal corresponding to an input operation from an external input device that is provided separately from the medical X-ray CT apparatus 100, and that outputs this electrical signal to the processing circuitry 37 is also included in examples of the input interface 31.

For example, the input interface 31 accepts an imaging condition of CT image data, a reconstruction condition at the time of reconstructing CT image data, an image processing condition for CT image data, and the like from the operator. Moreover, the input interface 31 accepts an operation to select an examination for the subject P. Furthermore, the input interface 31 accepts a specifying operation to specify a portion on an image.

The display 32 is a monitor that is referred to by an operator, and displays image data that is generated from CT image data to the operator, or displays a graphical user interface (GUI) to accept various kinds of instructions and settings and the like from the operator through the input interface 31 under control of the processing circuitry 37. Moreover, the display 32 displays a plan screen of a scanning plan, a screen during scanning, and the like.

The scan control circuitry 33 controls collection processing of projection data in the gantry 10 by controlling operation of the X-ray-irradiation control circuitry 11, the gantry driving circuitry 16, the data collecting circuitry 14, and the table driving device 21, under control of the processing circuitry 37. Specifically, the scan control circuitry 33 controls imaging to collect a positioning image (scano-image), and collection processing of projection data in actual imaging (scanning) to collect an image to be used for diagnosis.

The preprocessing circuitry 34 performs correction processing, such as logarithmic conversion processing, offset correction, sensitivity correction, and beam hardening correction, on the projection data generated by the data collecting circuitry 14, to generate corrected projection data. Specifically, the preprocessing circuitry 34 generates corrected projection data for each of the projection data of the positioning image that is generated by the data collecting circuitry 14 and projection data that is collected in the actual imaging, to store in the memory 35.

The memory 35 stores the projection data generated by the preprocessing circuitry 34. Specifically, the memory 35 stores the projection data of a positioning image, and the projection data for diagnosis collected in the actual imaging, generated by the preprocessing circuitry 34. Moreover, the memory 35 stores CT image data that is reconstructed by the image reconstructing circuitry 36 described later. Furthermore, the memory 35 stores, as necessary, a processing result by the processing circuitry 37 described later.

The image reconstructing circuitry 36 reconstructs X-ray-CT image data by using the projection data stored in the memory 35. Specifically, the image reconstructing circuitry 36 reconstructs CT image data from each of the projection data of the positioning image and the projection data of an image used for diagnosis. Various methods are available as a reconstruction method, and the back projection processing is one, for example. Moreover, as the back projection processing, for example, back projection processing by filtered back projection (FBP) can be applied. Alternatively, the image reconstructing circuitry 36 can reconstruct CT image data by using a method of successive approximation.

Furthermore, the image reconstructing circuitry 36 generates image data by performing various kinds of image processing on CT image data. The image reconstructing circuitry 36 stores the reconstructed CT image data, and the image data that is generated by various kinds of image processing in the memory 35.

The processing circuitry 37 performs overall control of the X-ray CT apparatus 100 by controlling operation of the gantry 10, the table device 20, and the console 30. Specifically, the processing circuitry 37 controls CT scanning performed in the gantry 10 by controlling the scan control circuitry 33. Moreover, the processing circuitry 37 controls the image reconstruction processing and the image generation processing in the console 30 by controlling the image reconstructing circuitry 36. Furthermore, the processing circuitry 37 controls to display various kinds of image data stored in the memory 35 on the display 32.

Moreover, the processing circuitry 37 performs a control function 37a, an analysis function 37b, an acquisition function 37c, a generation function 37d, and a display control function 37e as shown in FIG. 13. The control function 37a performs overall control of the X-ray CT apparatus 100, and performs processing similar to that of the control function 351 described above at generation of a color image. The analysis function 37b performs processing similar to that of the analysis function 352 described above. The acquisition function 37c performs processing similar to that of the acquisition function 353 described above. The generation function 37d performs processing similar to that of the generation function 354 described above. The display control function 37e performs processing similar to that of the display control function 355 described above.

Although the case in which the respective processing functions are implemented by single processing circuitry (the processing circuitry 350 and the processing circuitry 37) has been explained as an example in the above embodiments, the embodiments are not limited thereto. For example, the processing circuitry described above can be configured by combining multiple independent processors such that the respective processors implement the respective processing functions by executing respective programs. Furthermore, the respective processing functions of the processing circuitry described above can be implemented by distributing or integrating to a single or multiple processing circuits appropriately.

Moreover, the term "processor" used in the explanation of the respective embodiments described above signifies a central processing unit (CPU), a graphics processing unit (GPU), or a circuit such as an application specific integrated circuit (ASIC), a programmable logic device (for example, a simple programmable logic device (SPLD), and a complex programmable logic device (CPLD)), and a field programmable gate array (FPGA). The programs can be configured to be directly installed in a circuit of the processor, instead of storing the programs in the memory. In this case, the processor implements the functions by reading and executing the program installed in the circuit. The respective processors of the present embodiment are not limited to be configured as a single circuit per processor, but can be configured also as one processor by combining multiple independent circuits to implement the functions.

A medical image-processing program executed by a processor is installed in advance in a read only memory (ROM), a memory, and the like to be provided. The medical image-processing program can be recorded in a computer-readable recording medium, such as a compact disk (CD)-ROM, a flexible disk (FD), a CD-recordable (CD-R), and a digital versatile disk (DVD), in a file in a format enabling to be installed or executed in these apparatuses to be provided. Furthermore, the medical image-processing program can be stored in a computer connected to a network such as the Internet, and be provided or distributed by being downloaded through the network. For example, the medical image-processing program is configured with modules including the respective functions. As actual hardware, a CPU reads and executes the program from a storage medium such as a ROM, and the respective modules are thereby loaded on a main storage device, and created in the main storage device.

Furthermore, although it has been explained that a single unit of the memory 320 stores the programs corresponding to the respective processing functions in FIG. 2, it can be configured such that multiple memories are arranged in a distributed manner and the processing circuitry 350 reads a corresponding program from an individual memory. Moreover, although it has been explained that a single unit of the memory 35 stores the programs corresponding to the respective processing functions in FIG. 13, it can be configured such that multiple memories are arranged in a distributed manner and the processing circuitry 37 reads a corresponding program from an individual memory.

According to at least one of the embodiments explained above, a color image that facilitates observation of an index relating to blood flow can be displayed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image-processing apparatus comprising processing circuitry configured to
    acquire image data including a blood vessel of a subject,
    acquire an index value relating to blood flow at each position of the blood vessel by performing fluid analysis of a structure of the blood vessel included in the acquired image data,
    acquire switching information to switch color information for displaying the index value, the switching information being information that determines a situation in which the index value is to be displayed,
    change a color table to assign different colors according to a difference in the index value based on the switching information,
    generate a result image using the changed color table as an image indicating a blood vessel of the subject, and
    cause a display to display the result image.

2. The medical image-processing apparatus according to claim 1, wherein
    the processing circuitry is configured to set a reference value of the index value according to the switching information, and generate a color image in which colors are varied at the set reference value as a boundary.

3. The medical image-processing apparatus according to claim 1, wherein the processing circuitry is configured to set a reference value of the index value according to the switching information, and generate a color image in which brightness of a color is changed at the set reference value as a boundary.

4. The medical image-processing apparatus according to claim 1, wherein
the processing circuitry is configured to set a reference value of the index value according to the switching information, and generate a color image in which transparency is changed at the set reference value as a boundary.

5. The medical image-processing apparatus according to claim 2, wherein
the processing circuitry is configured to set the reference value for each type of the index value included in the switching information.

6. The medical image-processing apparatus according to claim 2, wherein
the processing circuitry is configured to generate a color image in which an index value within a predetermined range based on the reference value among the index values is emphasized.

7. The medical image-processing apparatus according to claim 1, wherein
the processing circuitry is configured to generate a color image which an internal portion of the blood vessel in the image indicating the blood vessel of the subject is expressed by a color corresponding to an index value relating to blood flow at each position.

8. The medical image-processing apparatus according to claim 1, wherein
the processing circuitry is configured to generate a color image which a line along the blood vessel in the image indicating the blood vessel of the subject is expressed by a color corresponding to an index value relating to blood flow at each position in a direction of length of the blood vessel.

9. The medical image-processing apparatus according to claim 1, wherein
the processing circuitry is configured to acquire examination information that indicates whether an examination for the subject is urgent examination or a normal examination different from the urgent examination, as the switching information.

10. The medical image-processing apparatus according to claim 1, wherein
the processing circuitry is configured to acquire examination information that indicates a total number of times of an examination to acquire an index of blood flow for the subject, as the switching information.

11. The medical image-processing apparatus according to claim 1, wherein
the processing circuitry is configured to acquire subject information that indicates a body type of the subject, as the switching information.

12. The medical image-processing apparatus according to claim 1, wherein
the processing circuitry is configured to acquire examination information that indicates an examination result of the subject, as the switching information.

13. The medical image-processing apparatus according to claim 1, wherein
the processing circuitry is configured to acquire information of an image to be displayed along with the index value, as the switching information.

14. The medical image-processing apparatus according to claim 13, wherein
the processing circuitry is configured to acquire information of a position that is specified on the image, as the switching information.

15. The medical image-processing apparatus according to claim 1, wherein
the processing circuitry is configured to acquire information of an application to be used together with display of the index value, as the switching information.

16. The medical image-processing apparatus according to claim 1, wherein
the processing circuitry is configured to acquire information indicating a purpose of displaying the index value, as the switching information.

17. The medical image-processing apparatus according to claim 1, wherein
the processing circuitry is configured to
acquire a position on the blood vessel at which an index value is an identical value to a reference value of the index value among index values at respective positions of the blood vessel, as the switching information, and
generate a color image in which color arrangement is changed according to the acquired position on the blood vessel.

18. An X-ray computerized-tomography (CT) apparatus comprising
processing circuitry configured to
acquire image data including a blood vessel of a subject,
acquire an index value relating to blood flow at each position of the blood vessel by performing fluid analysis of a structure of the blood vessel included in the acquired image data,
acquire switching information to switch color information for displaying the index value, the switching information being information that determines a situation in which the index value is to be displayed,
change a color table to assign different colors according to a difference in the index value based on the switching information,
generate a color image using the changed color table as an image indicating a blood vessel of the subject, and
cause a display to display the color image.

19. A medical image-processing method comprising:
acquiring image data that includes a blood vessel of a subject;
acquiring an index value relating to blood flow at each position of the blood vessel by performing fluid analysis of a structure of the blood vessel included in the acquired image data;
acquiring switching information to switch color information for displaying the index value, the switching information being information that determines a situation in which the index value is to be displayed;
changing a color table to assign different colors according to a difference in the index value based on the switching information;
generating a color image using the changed color table as an image indicating a blood vessel of the subject; and
causing a display to display the color image.

* * * * *